United States Patent
Stork genannt Wersborg

(10) Patent No.: US 11,013,237 B2
(45) Date of Patent: May 25, 2021

(54) HEAT TREATMENT MONITORING SYSTEM

(71) Applicant: Ingo Stork genannt Wersborg, Munich (DE)

(72) Inventor: Ingo Stork genannt Wersborg, Munich (DE)

(*) Notice: Subject to any disclaimer, the term of this patent is extended or adjusted under 35 U.S.C. 154(b) by 0 days.

(21) Appl. No.: 16/790,825

(22) Filed: Feb. 14, 2020

(65) Prior Publication Data

US 2020/0178543 A1  Jun. 11, 2020

Related U.S. Application Data

(63) Continuation of application No. 14/649,454, filed as application No. PCT/EP2013/003662 on Dec. 4, 2013, now abandoned.

(30) Foreign Application Priority Data

Dec. 4, 2012 (EP) ..................................... 12008113
Oct. 4, 2013 (EP) ..................................... 13004786

(51) Int. Cl.
*A21B 1/40* (2006.01)
*A21B 3/10* (2006.01)
(Continued)

(52) U.S. Cl.
CPC ................. *A21B 1/40* (2013.01); *A21B 3/10* (2013.01); *A21C 13/00* (2013.01); *F24C 7/08* (2013.01); *F24C 7/087* (2013.01); *F24C 15/008* (2013.01); *F24C 15/04* (2013.01); *G01J 5/0044* (2013.01); *G01N 33/02* (2013.01)

(58) Field of Classification Search
CPC .. A21B 1/40; A21B 3/10; A21C 13/00; F24C 7/08; F24C 7/087; F24C 15/008; F24C 15/04; G01J 5/0044; G01N 33/02
See application file for complete search history.

(56) References Cited

U.S. PATENT DOCUMENTS 1,774,433 A * 8/1930 Gardiner ................ G05D 23/27
                                                            99/331
3,486,694 A * 12/1969 Henson .............. G05D 23/1919
                                                            236/15 R
(Continued)

FOREIGN PATENT DOCUMENTS

DE          19831635 A1    1/2000
DE     10 2005 030483       6/2005
(Continued)

OTHER PUBLICATIONS

International Search Report issued in corresponding PCT International Application No. PCT/EP2013/003662.
(Continued)

*Primary Examiner* — Kyle R Quigley
(74) *Attorney, Agent, or Firm* — Bejin Bieneman PLC

(57) ABSTRACT

A heat treatment monitoring system comprises a sensor unit having at least one sensor to determine current sensor data of food being heated; a processing unit to determine current feature data from the current sensor data; and a monitoring unit adapted to determine a current heating process state in a current heating process of the monitored food by comparing the current feature data with reference feature data of a reference heating process.

13 Claims, 18 Drawing Sheets

(51) Int. Cl.
*F24C 15/00* (2006.01)
*A21C 13/00* (2006.01)
*F24C 7/08* (2006.01)
*F24C 15/04* (2006.01)
*G01J 5/00* (2006.01)
*G01N 33/02* (2006.01)

(56) References Cited

U.S. PATENT DOCUMENTS

| | | | |
|---|---|---|---|
| 3,536,405 A | | 10/1970 | Flower |
| 3,895,870 A | | 7/1975 | Cullen et al. |
| 4,744,407 A | * | 5/1988 | Fishman .............. B22D 37/00 164/155.2 |
| 5,157,254 A | * | 10/1992 | Anderson ............ G01N 21/474 250/239 |
| 5,786,568 A | | 7/1998 | McKinney |
| 6,080,972 A | | 6/2000 | May |
| 6,397,734 B1 | | 6/2002 | Atzinger |
| 2004/0197012 A1 | | 10/2004 | Bourg, Jr. |
| 2004/0206248 A1 | * | 10/2004 | Lawson ................ G01N 21/27 99/388 |
| 2006/0007531 A1 | * | 1/2006 | Korengut ........... G01N 21/9501 359/362 |
| 2006/0081135 A1 | * | 4/2006 | Britton .................... A21B 7/00 99/486 |
| 2006/0112833 A1 | | 6/2006 | Blaschke |
| 2008/0216812 A1 | | 9/2008 | Dougherty |
| 2009/0017173 A1 | * | 1/2009 | Kozman ................ G01N 33/10 426/233 |
| 2009/0251591 A1 | * | 10/2009 | Whitham ............. H04N 5/2353 348/362 |
| 2010/0055259 A1 | | 3/2010 | Bourg, Jr. |
| 2011/0002677 A1 | * | 1/2011 | Cochran ............ A47J 37/0623 392/416 |
| 2011/0123689 A1 | | 5/2011 | Luckhardt et al. |
| 2012/0132636 A1 | | 5/2012 | Moore |

FOREIGN PATENT DOCUMENTS

| | | |
|---|---|---|
| DE | 102007063041 A1 | 7/2009 |
| DE | 10 2008 009660 | 8/2009 |
| DE | 10 2010 016651 | 10/2011 |
| DE | 20 2011 002570 | 5/2012 |
| EP | 0 250 169 | 12/1987 |
| EP | 0529222 A2 | 3/1993 |
| EP | 0 563 698 | 10/1993 |
| EP | 0 701 387 | 3/1996 |
| EP | 1 595 453 | 11/2005 |
| EP | 2149755 A1 | 2/2010 |
| EP | 2515044 A1 | 10/2012 |
| EP | 2 520 169 | 11/2012 |
| JP | 2001-330257 | 11/2001 |
| JP | 02-157526 | 5/2002 |
| JP | 04-020311 | 1/2004 |
| JP | 2006-149593 | 6/2006 |
| JP | 2009-175141 | 8/2009 |
| JP | 2010-127545 | 6/2010 |
| JP | 2011-506022 | 3/2011 |
| JP | 2011-149606 | 8/2011 |
| JP | 2011-251028 | 12/2011 |
| JP | 2012-047735 | 3/2012 |
| JP | 2012-113708 | 6/2012 |
| JP | 2012-151732 | 8/2012 |
| JP | 2012-217102 | 11/2012 |
| WO | WO 03/030645 A1 | 4/2003 |
| WO | 2006101531 A1 | 9/2006 |
| WO | 2008016309 A1 | 2/2008 |
| WO | 2011053601 A2 | 5/2011 |

OTHER PUBLICATIONS

Jan Peters and Stefan Schaal. "Natural Actor-Critic" Science Direct, Neurocomputing 71 (2008), p. 1180-1190.
European Office Action dated Aug. 25, 2016.
European Office Action dated Aug. 9, 2017.
Chinese First Office Action dated Jun. 2, 2017.
Chinese First Office Action dated Jun. 2, 2017 (in Chinese).
Japanese Office Action dated Oct. 24, 2017 issued in JP patent application 2015-545691 (English translation).
Japanese Notice of Reasons for Refusal.
Indian Office Action dated Aug. 22, 2019.
Ross McKitrick, Understanding Principal Components and the MBH98 Results, Universtiy of Guelph, 2005.
Japanese Office Action dated Jun. 25, 2018 in JP patent application 2015-545691 (English translation).
European Search Report dated Jun. 26, 2019.
European Office Action dated Apr. 20, 2020.

* cited by examiner

300

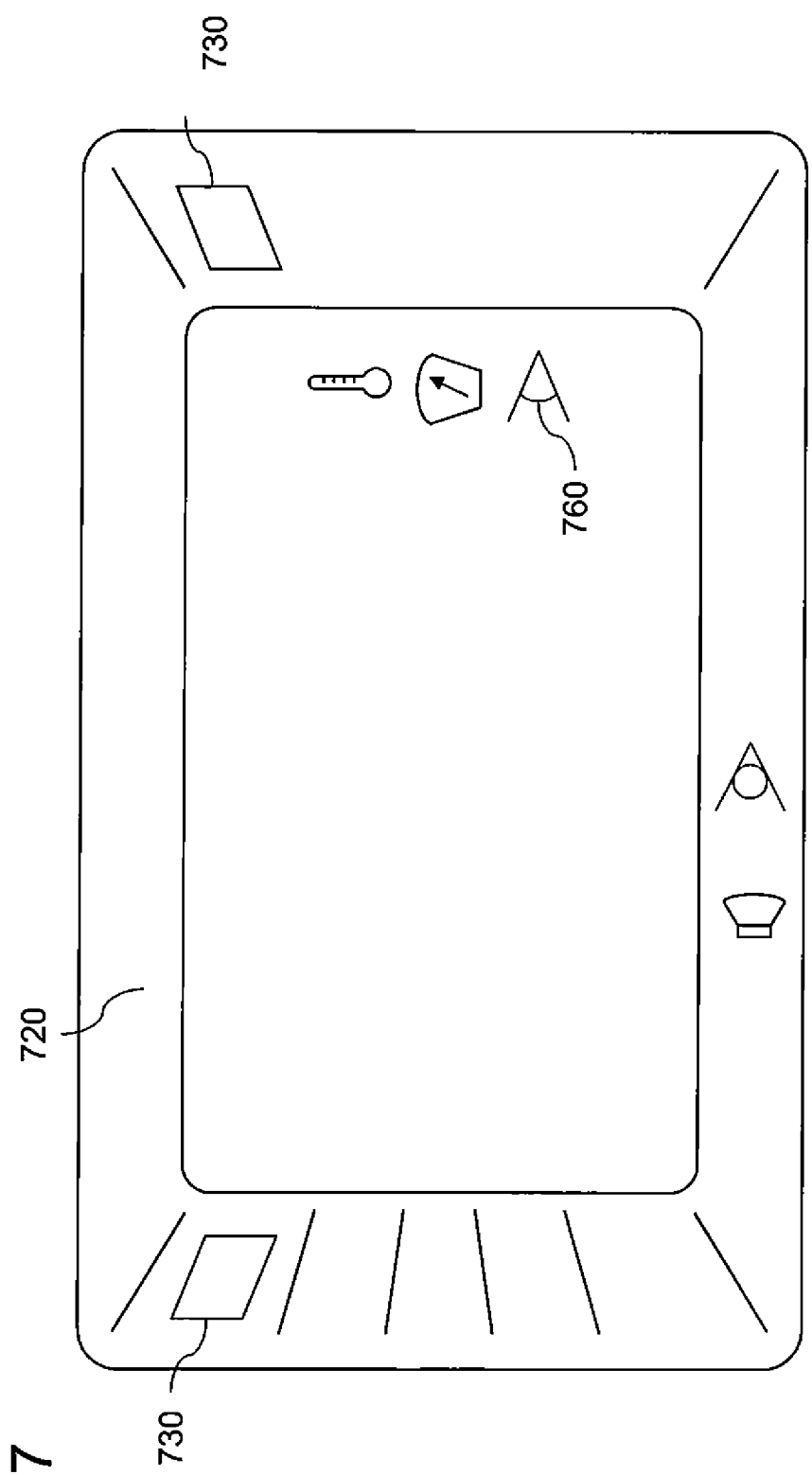

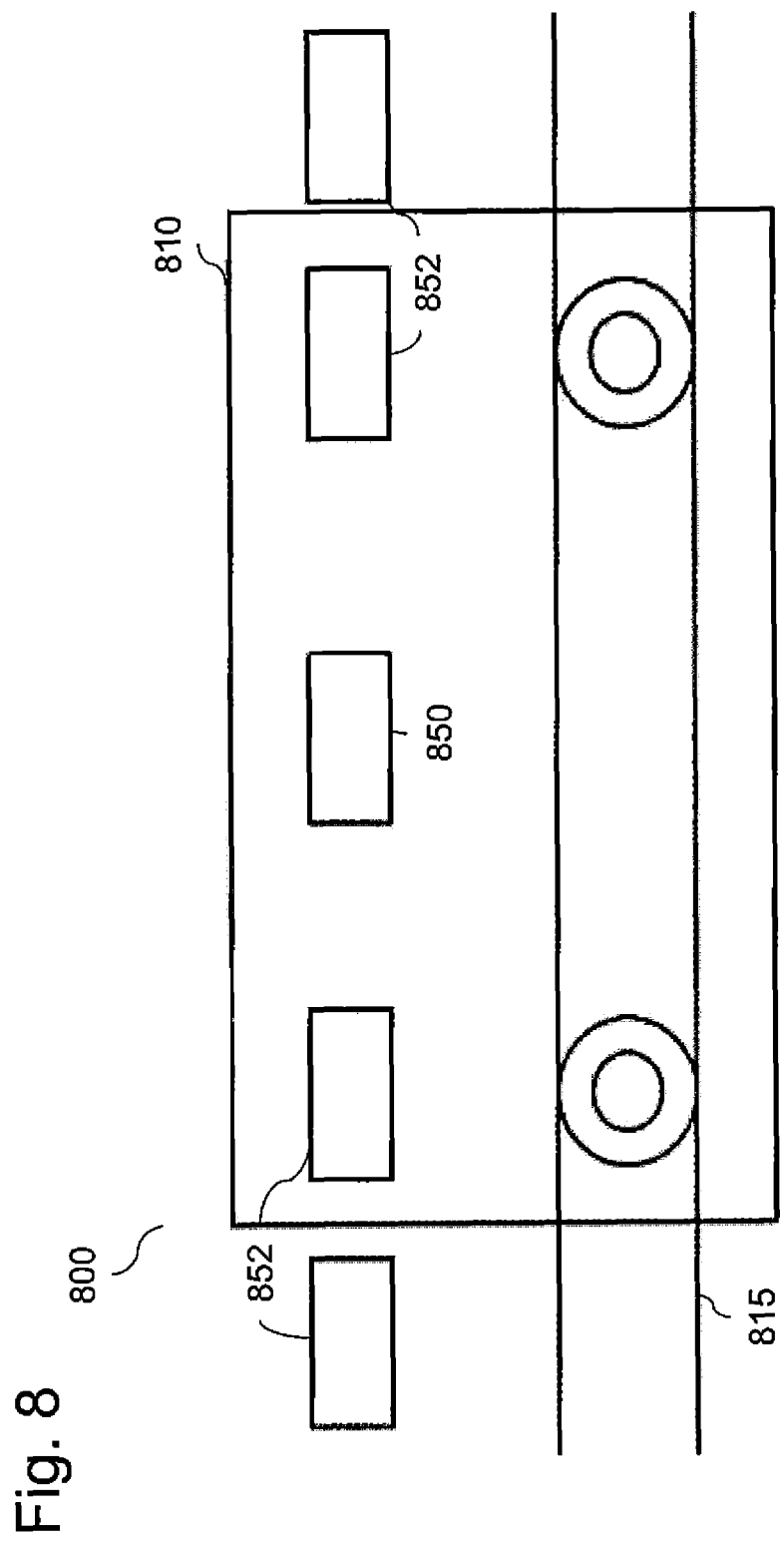

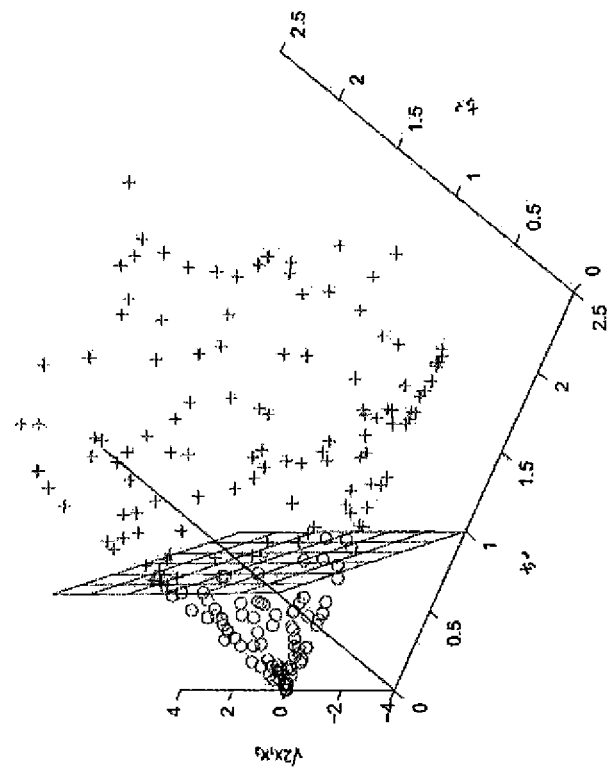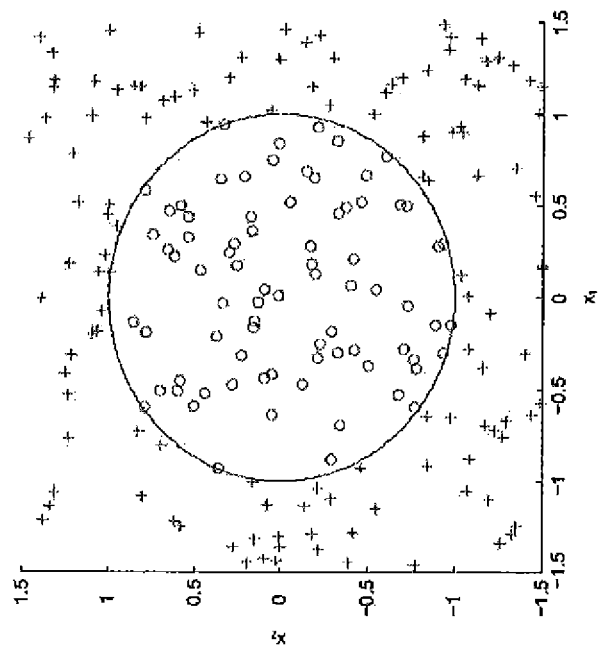
Fig. 16

HEAT TREATMENT MONITORING SYSTEM

CROSS-REFERENCE TO RELATED APPLICATIONS

This application is a continuation of application Ser. No. 14/649,454, filed Jun. 3, 2015, which is a National Stage entry under 35 U.S.C. § 371 of International Application No. PCT/EP2013/003662, filed on Dec. 4, 2013, published on Jun. 12, 2014 under Publication Number WO 2014/086486 A2, which claims the benefit of priority under 35 U.S.C. § 119 of European Patent Application Number 13004786.3 filed Oct. 4, 2013; and European Patent Application Number 12008113.8, filed Dec. 4, 2012.

The present invention is related to a heat treatment monitoring system, in particular a monitoring system for heating, baking or proofing of food to be heated like bread, dough or the like.

Treating food with heat is done by mankind probably since the invention of fire. However, up until now this task is still controlled by a human operator. The goal of the underlying invention is to automate the food treatment and in particular bread baking or proofing such that no human interaction is necessary.

Many inventions are known that get close to this goal. For instance, DE 10 2005 030483, describes an oven for heat treatment with an opening device that can be opened or closed automatically. In DE 20 2011 002570, an apparatus for heat treatment of food products and receiving them on a product carrier is stated. The latter is equipped with a control system for controlling a treatment process for detecting the type and amount of products. The controller selects with predefined data to perform an automatic identification of the products. A camera outside of the treatment chamber may be used as sensor. In EP 250 169 A1, a baking oven door is described that incorporates a camera to visualize a muffle or baking chamber. The visualization is of advantage to save energy losses created by looking windows. US 0 2011 0123 689 describes an oven that comprises a camera and a distance sensor in order to extract product features for heating processes. DE 20 2011 002 570 U1 describes a system with sensor acquisition in ovens.

However, still the heat treatment of food in particular for baking bread with an oven follows manual setup and happens under human supervision. When a human operator puts bread into an oven, important properties such as temperature, time, and circulation have to be set. Usually the settings are stored within a database of oven control programs. A human operator has to pick the appropriate program and this still is source of error and creates human labor with a certain degree of know how. Further, many process parameters may lead to an undesired food product outcome. Bread may be under baked or over baked, even if the correct program has been chosen. This may be caused by differences in oven pre-heating, dough preparation, outside temperature, outside humidity, load distribution, oven door opening times and many more. It still requires skilled human labor to supervise baking or food heat treatment.

Moreover, when processing food as e.g. in a manufacturing plant for raw or prebaked dough, the objects being processed underlie many process variations. Due to the nature of many food products, the objects being processed may vary in shape, colour, size and many other parameters. This is one of the key challenges in industrial food processing, because often processing devices have to be adjusted to compensate these variations. Hence, it is desirable to automate the industrial processing steps, making manual adjustments ideally unnecessary. In baking, for instance changes in flour characteristics may result in severe process variations of industrial dough processing devices. For instance it may be necessary to adapt parameters of a mixer, a dough divider, dough forming devices, proofing, cutter, packaging, the baking program of an oven or a vacuum baking unit.

In order to achieve the goal of automated baking or food processing it is necessary to provide the corresponding monitoring system with data from suitable monitoring devices. Hence, there is a need for monitoring systems with monitoring devices for collecting suitable data.

For goods baked in an oven a monitoring system with a camera may be used to monitor the baking process through a window in an oven. However, in order to prevent thermal losses by heat dissipation through the window, in conventional ovens such looking windows are made of double glass, i.e. they have an inner and an outer glass pane. Hence, light from outside the oven may pass the outer glass pane and be reflected into the camera by the inner glass pane, leading to disturbed images of the baked goods.

It is therefore desirable to provide a heat treatment monitoring system that reduces disturbances of images of the baked goods captured through a double glass window.

In food processing systems data concerning the structure of the processed food should be obtained without stopping the food processing, in order to not reduce a production output. It is hence desirable to adjust the parameters of the aforementioned devices of a food processing system or any other device in food processing, based on contactless measurement techniques.

In order to make data captured by monitoring devices useful for automated baking or food processing it is desirable to provide a method for classifying a multitude of images recorded by monitoring devices observing a processing area of processed food and to provide a machine using the same.

Once the data are suitably classified it is desirable to take advantage of cognitive capabilities in order to increase the heat treatment machine in flexibility, quality, and efficiency. This can be further separated in the objects:

It is desirable to provide a system being able to gain knowledge by learning from a human expert how to abstract relevant information within food processing and how to operate an oven, wherein the system should show reasonable behavior in unknown situations and should be able to learn unsupervised.

It is desirable to provide a system increasing the efficiency by closed-loop control of energy supply adapting to changes in processing time and maintaining a desired food processing state.

It is desirable to provide a system having flexibility for individually different food processing tasks by adapting to different types of food or process tasks.

These objectives are achieved by a heat treatment monitoring system according to the appended claims.

In particular, to capture image from a heat treatment chamber (oven) it is advantageous to use an illumination in combination with outside window tinting or darkening. This provides less impact of outside light to the image processing of the oven inside pictures. It is recommended to tint the window by at least 40%.

For industrial food processing it is advantageous to use a laser line generator, or any other light source, and a camera sensor, or any other optical sensor, to grasp information about the food being processed. With a procedure, also known as laser triangulation, a laser line may be projected onto a measurement object, in order to obtain its characteristics.

Moreover, it is advantageous that the heat treatment of food is automated such that no further human interaction is necessary besides loading and unloading the oven or the heat treatment machine. However, even this step may be automated, if desired. In order to do so the heat treatment machine needs a treatment chamber that is camera monitored and equipped with an inside treatment chamber temperature sensor such as a thermometer. Instead of using a camera an array of at least two photodiodes may also be used. It is advantageous to use more sensors acquiring signals related to inside treatment chamber humidity, time, ventilation, heat distribution, load volume, load distribution, load weight, temperature of food surface, and interior temperature of the treated food. The following sensors may as well be applied: hygrometer, laser triangulation, insertion temperature sensors, acoustic sensors, scales, timers, and many more. Further, cooling systems attached to any heat sensible sensor applied may be applied. For instance, this may be an electrical, air or water cooling system such as a Peltier cooler or ventilator, a thermoelectric heat pump, or a vapor-compression refrigeration, and many more.

Further it is advantageous that in a heat treatment process of food and in particular of baked goods with a heat treatment machine, such as an oven with heat treatment chamber, the inside temperature and the interior camera image or other sensors can be used for the control of power supply or treatment parameters. According to the invention, the camera image is suitable for the detection of parameters related to the changing volume and/or the color of the food during heating of these. According to a model machine learned or fixed prior to this, it can be determined with this method for the heat treatment machine, if the treated food is in a predefined desired process state, and with a closed-loop control of the power of the heat treatment process the process may be individually adjusted. The desired process result may be reached at several locally distributed heat treatment machines by distributing the parameters defined by the desired process conditions of the treated food. Moreover, the sensors used and the derived process data, in particular the camera image, may be used to determine the type and quantity of the food based on the data characteristics and thus to start appropriate process variants automatically.

According to an embodiment of the present invention, a heat treatment monitoring system comprises: a heat treatment machine comprising a heat treatment chamber, a double glass window comprising an inside window and an outside window, and an illumination apparatus for illuminating the inside of the heat treatment chamber, and a monitoring apparatus mounted to the heat treatment machine and comprising a camera to observe the inside of the heat treatment chamber through the inside window, wherein the visible transmittance of the outside window is lower than the visible transmittance of the inside window to reduce reflections within the double glass window structure and outside illumination effects on image processing of images recorded by the camera. Preferably, the outside window is darkened by a coating. Preferably, a metal foil or a tinting foil is applied at the outside window. Preferably, the outside window comprises a tinted glass. Preferably, the outside window has a maximum visible transmittance of 60% Preferably, the double glass window is a heat treatment machine door window of a heat treatment machine door of the heat treatment machine. Preferably, the monitoring apparatus is adapted to generate high dynamic range (HDR) processed images of the food to be heated within the heat treatment chamber. Preferably, the monitoring apparatus further comprises a casing and a camera sensor mount, to which the camera is mounted. Preferably, the casing is equipped with heat sinks and fans to provide cooling of the camera. Preferably, the heat treatment machine is a convection or a deck oven having at least two trays arranged in a stacked manner. Preferably, the camera is tilted in such a way in a horizontal and/or a vertical direction with regard to the double glass window to be adapted to observe at least two trays at once in the convection or deck oven. Preferably, the heat treatment monitoring system comprises at least two cameras to observe each tray separately. Preferably, the heat treatment monitoring system further comprises a control unit being adapted to process and classify the images of food observed by the camera based on training data for determining an end time of a heating process for the food. Preferably, the control unit is adapted to stop the heating of the heat treatment machine when the heating process has to be ended. Preferably, the control unit is adapted to open automatically the heat treatment machine door when the baking process has to be ended, or wherein the control unit is adapted to ventilate the heat treatment chamber with cool air or air when the heating process has to be ended.

According to another embodiment of the present invention, a heat treatment monitoring system comprises a sensor unit having at least one sensor to determine current sensor data of food being heated; a processing unit to determine current feature data from the current sensor data; and a monitoring unit adapted to determine a current heating process state in a current heating process of the monitored food by comparing the current feature data with reference feature data of a reference heating process. Preferably, the heat treatment monitoring system further comprises a learning unit adapted to determine a mapping of current sensor data to current feature data and/or to determine reference feature data of a reference heating process based on feature data of at least one training heating process. Preferably, the learning unit is adapted to determine a mapping of current sensor data to current feature data by means of a variance analysis of at least one training heating process to reduce the dimensionality of the current sensor data. Preferably, the learning unit is adapted to determine a mapping of current feature data to feature data by means of a variance analysis of at least one training heating process to reduce the dimensionality of the current feature data. Preferably, the variance analysis comprises at least one of principal component analysis (PCA), isometric feature mapping (ISOMAP) or linear Discriminant analysis (LDA) or a dimensionality reduction technique. Preferably, the learning unit is adapted to determine reference feature data of a reference heating process by combining predetermined feature data of a heating program with a training set of feature data of at least one training heating process being classified as being part of the training set by an user preference. Preferably, the heat treatment monitoring system further comprises a recording unit to record current feature data of a current heating process, wherein the learning unit is adapted to receive the recorded feature data from the recording unit to be used as feature data of a training heating process. Preferably, the sensor unit comprises a camera recording a pixel image of food being heated, wherein the current sensor data of the camera corresponds to the current pixel data of a current pixel image. Preferably, the current pixel data comprises first pixel data corresponding to a first color, second pixel data corresponding to a second color, and third pixel data corresponding to a third color. Preferably, the first, second and third color corresponds to R,G and B, respectively. Preferably, the camera is adapted to generate HDR processed pixel images as current pixel data. Preferably, the heat treatment monitoring system further comprises a classification unit adapted to classify the type of food to be heated and to choose a reference heating process corresponding to the determined type of food. Preferably, the heat treatment monitoring system further comprises a control unit adapted to change a heating process from a proofing process to a baking process based on a comparison of the current heating process state determined by the monitoring unit with a predetermined heating process state. Preferably, the heat treatment monitoring system further comprises a control unit adapted to control a display unit being adapted to indicate a remaining time of the heating process based on a comparison of the current heating process state determined by the monitoring unit with a predetermined heating process state corresponding to an end point of heating and/or to display images of the inside of the heat treatment chamber. Preferably, the heat treatment monitoring system further comprises a control unit adapted to alert a user, when the heating process has to be ended. Preferably, the heat treatment monitoring system further comprises a control unit adapted to control a temperature control of a heating chamber, means to adapt humidity in the heat treatment chamber by adding water or steam, a control of the ventilating mechanism, means for adapting the fan speed, means for adapting the differential pressure between the heat treatment chamber and the respective environment, means for setting a time dependent temperature curve within the heat treatment chamber, means for performing and adapting different heat treatment procedures like proofing or baking, means for adapting internal gas flow profiles within the heat treatment chamber, means for adapting electromagnetic and sound emission intensity of respective electromagnetic or sound emitters for probing or observing properties of the food to be heated. Preferably, the at least one sensor of the sensor unit comprises at least one of hygrometer, insertion temperature sensor, treatment chamber temperature sensor, acoustic sensors, scales, timer, camera, image sensor, array of photodiodes, a gas analyser of the gas inside the treatment chamber, means for determining temperature profiles of insertion temperature sensors, means for determining electromagnetic or acoustic process emissions of the food to be treated like light or sound being reflected or emitted in response to light or sound emitters or sources, means for determining results from 3D measurements of the food to be heated including 3D or stereo camera systems or radar, or means for determining the type or constitution or pattern or optical characteristics or volume or the mass of the food to be treated According to another embodiment of the present invention, a heat treatment monitoring system is provided, comprising: a heat treatment or baking unit for baking or proofing goods or food to be heated or a food processing line; a laser light distribution unit for generating a first laser beam and a second laser beam and for directing the first laser beam and the second laser beam to a position of baking goods within the baking unit; a first light detection unit for detecting the reflection of the first laser beam scattered from the baking goods; a second light detection unit for detecting the reflection of the second laser beam scattered from the baking goods; a measurement unit for determining a height profile of the baking goods according to the detections of the first light detection unit and the second detection unit; and a moving unit for changing a distance between the laser light distribution unit and the baking goods. Herein, the laser light distribution unit preferably comprises: a first laser light generating unit for generating the first laser beam; and a second laser light generating unit for generating the second laser beam. Further, the laser light distribution unit preferably comprises: a primary laser light generating unit for generating a primary laser beam; an optical unit for generating the first laser beam and the second laser beam from the primary laser beam. The optical unit preferably comprises: a movable and rotatable mirror, towards which the primary laser beam is directed, for generating the first laser beam and the second laser beam alternately by moving and rotating with respect to the primary laser light generating unit. The optical unit preferably comprises: a semi-transparent mirror, towards which the primary laser beam is directed, for generating the first laser beam and a secondary laser beam; and a mirror, towards which the secondary laser beam is directed, for generating the second laser beam. The first laser beam is preferably directed towards a first position; the second laser beam is preferably directed towards a second position; a piece of baking good is preferably moved from the first position to the second position by the moving unit; and a change of the height profile of the piece of baking good is preferably determined by the measurement unit. Preferably, the first laser beam is directed to a first end of a piece of baking good and has an inclination of less than 45° with respect to a support of the piece of baking good; the second laser beam is directed to a second end of the piece of baking good opposite to the first end and has an inclination of less than 45° with respect to the support; and the minimum angle between the first laser beam and the second laser beam is greater than 90°. Preferably, the moving unit is a conveyor belt that moves the baking goods through the baking unit. Preferably, the laser light distribution unit is located within the baking unit; and the first and second laser beams are directed directly from the laser light distribution unit towards the baking goods. Preferably, the laser light generating units are located outside the baking unit; and the laser beams are directed towards the baking goods by deflection mirrors. Preferably, the light detection units are located outside the baking unit; and the reflection of the laser beams is guided to the light detection units by guiding mirrors. Preferably, the mirrors are heated. Preferably, the first and second laser beams are fan shaped; and the reflection of the first and second laser beams are focused on the first and second light detection units by lenses. Preferably, the optical system constituted by the laser light distribution unit, the baking goods, and the light detection units satisfies the Scheimpflug principle. A method for monitoring baking of the present invention comprises the steps of: processing baking goods in a baking unit; moving the baking goods through the baking unit; generating a first laser beam and a second laser beam and directing the first laser beam and the second laser beam to a position of baking goods within the baking unit; detecting the reflection of the first laser beam scattered from the baking goods; detecting the reflection of the second laser beam scattered from the baking goods; and determining a height profile of the baking goods according to the detections of the scattered first and second laser beams.

The accompanying drawings, which are included to provide a further understanding of the invention and are incorporated in and constitute a part of this application, illustrate embodiment(s) of the invention and together with the description serve to explain the principle of the invention. In the drawings:

FIG. 7 shows a schematic view of an embodiment of a heat treatment chamber.

FIG. 8 shows a schematic view of an embodiment of a food production system.

FIG. 16 shows a mapping of two-dimensional test data to a three-dimensional space with an optimal linear separator.

FIGS. 1A and 1B illustrate a heat treatment monitoring system 100 according to an embodiment of the present invention. FIG. 1A illustrates a schematic cross-sectional top view of the heat treatment monitoring system 100, while FIG. 1B illustrates a schematic front view thereof.

Figure 1A:
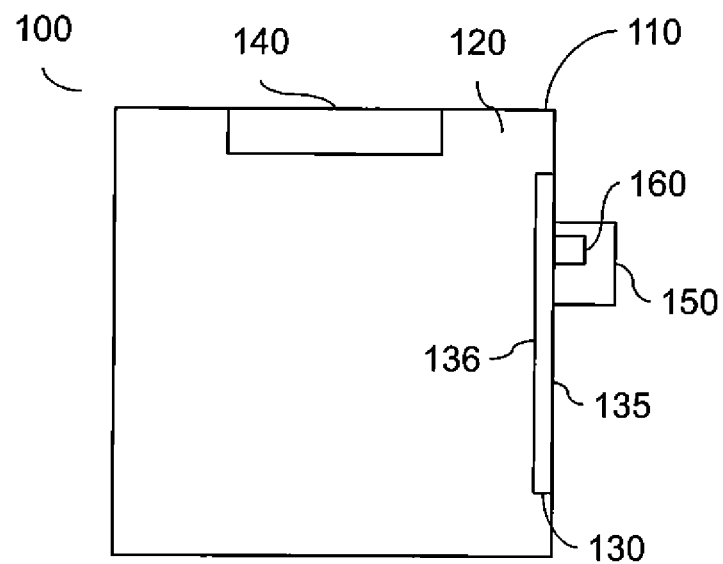
FIGS. 1A and 1B show a schematic cross sectional view and a schematic side view of an embodiment of a heat treatment monitoring system.
Figure 1B:
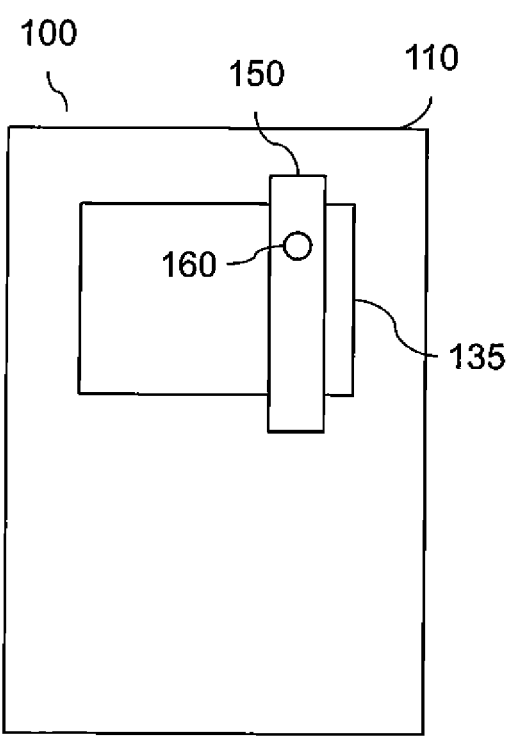

As illustrated in FIGS. 1A and 1B the heat treatment monitoring system or baking monitoring system or proofing and/or baking monitoring system 100 has an oven 110 with a heat treatment or oven chamber 120, at least one double glass window 130 at a side wall of the oven 110 and an illumination apparatus 140 inside the oven chamber 120.

The heat treatment machine or oven 110 may be any oven that may be conventionally used for cooking of food, in particular for baking or proofing of bread. The oven may cook food using different techniques. The oven may be a convection type oven or a radiation type oven.

The heat treatment or oven chamber 120 captures most of the interior of the oven 110. Inside the oven chamber 120 food is cooked. The food may be placed on a differing number of trays which can be supported at the oven chamber walls. The food may also be placed on moveable carts with several trays, which can be moved inside the oven chamber 120. Inside the oven chamber 120 a heat source is provided, which is used to cook the food. Moreover, also a ventilation system may be comprised inside the oven chamber to distribute the heat produced by the heat source more evenly.

The inside of the oven or heat treatment chamber gets illuminated by an illumination apparatus 140. The illumination apparatus 140 may be arranged inside the oven or heat treatment chamber as shown in FIG. 1A. The illumination apparatus 140 may also be located outside the oven chamber 120 and illuminate the oven chamber 120 through a window. The illumination apparatus 140 may be any conventional light emitting device, e.g. a light bulb, a halogen lamp, a photodiode or a combination of several of these devices. The illumination apparatus 140 may be focused on the food to be cooked inside the oven chamber 120. In particular, the illumination apparatus 140 may be adjusted or focused such that there is a high contrast between the food to be cooked and the surrounding interior of the oven chamber 120 or between the food and tray and/or carts on which the food is located. Such a high contrast may be also supported or generated solely by using special colors for the light emitted by the illumination apparatus 140.

In a wall of the oven chamber 120 a window is provided. In order to prevent a loss of heat out of the oven chamber 120, the window is preferably a double glass window 130 having an outer glass pane or outside window 135 and an inner glass pane or inside window 136. The double glass window 130 may prevent heat dissipation between the inside window 136 and the outside window 135 by providing a special gas or a vacuum between the inside window 136 and the outside window 135. The double glass window 130 may also be cooled by air ventilation between the inside window 136 and the outside window 135 to prevent a heating of the outside window 135, wherein no special gas or a vacuum is provided between the inside window 136 and the outside window 135. The illumination apparatus 140 may be also be provided between the inside window 136 and the outside window 135. The outer glass surface of the outside window 135 is less hot and thus suitable for mounting a camera 160. It may be further beneficial to use an optical tunnel between the inside window 136 and the outside window 135, because this again reduces reflections and heat impact.

Through the double glass window 130 a cooking or baking procedure inside the oven chamber 120 may be observed from outside the heat treatment machine or oven.

As is illustrated in FIG. 1B a monitoring apparatus 150 is mounted on the heat treatment machine or oven 110. The monitoring apparatus 150 is mounted across the outside window 135 of the double glass window 130 and comprises a camera 160 arranged next to the outside window 135, which is used to observe the food inside the oven chamber 120 during cooking or baking. The camera 160 may be any conventional camera which is able to provide image data in a computer accessible form. The camera 160 may for example be charged coupled device (CCD) camera or a complementary metal-oxide-semiconductor (CMOS) camera. The camera 160 obtains images of the cooked food during the cooking procedure. As will be described below these images may be used for automatically controlling the cooking or baking procedure. Although the camera 160 is preferably mounted at an outside of the outside window 135 to be easily integrated within the monitoring apparatus 150, wherein the camera 160 then observes an inside of the heat treatment chamber 120 through the double glass window 130, the camera 160 may also be provided between the inside window 136 and the outside window 135 to observe an inside of the heat treatment chamber through the inside window 136.

However, a problem arises if an external light source is present outside of the oven chamber 120 in front of the double glass window 130.

Figure 2A:
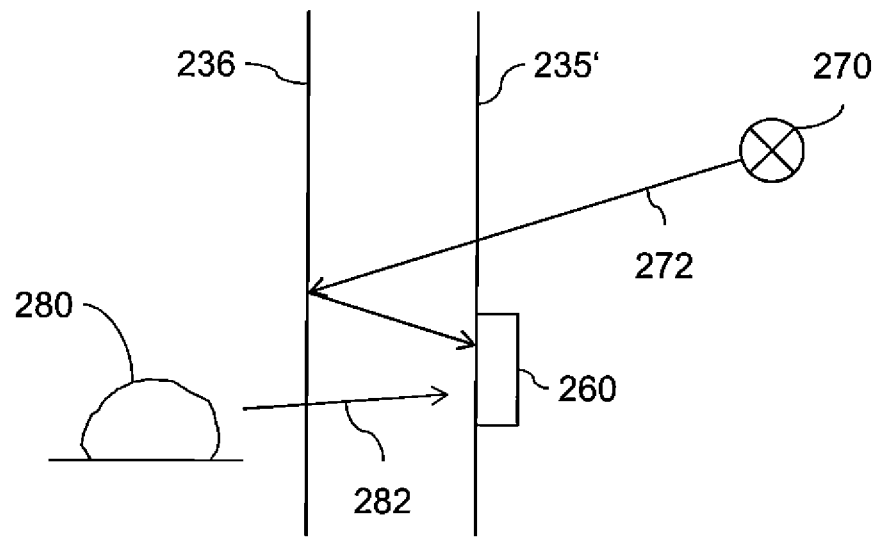
FIGS. 2A and 2B show the reflection properties of a conventional double glass window and a double glass window of an embodiment of a heat treatment monitoring system.
Figure 2B:
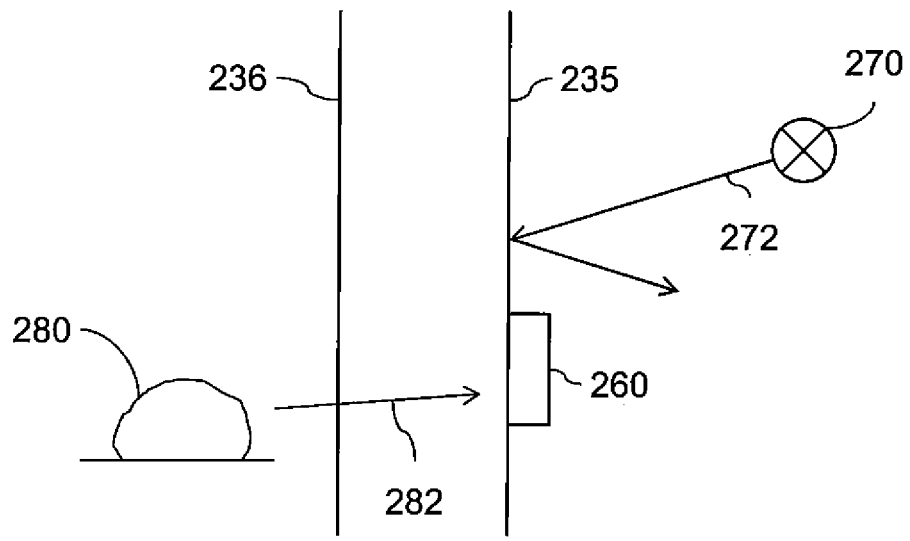

As illustrated in FIG. 2A, irritating light 272 emitted by an external light source 270 may pass through an outside window 235' of a double glass window, but might be reflected by the inside window 236 into a camera 260 observing food 280 to be cooked. Therefore, the camera 260 does not only obtain light 282 emitted or reflected from the food 280, but also the irritating light 272, reflected at the inside wall 236. This result in a deterioration of the image data provided from the camera 260 and may therefore adversely affect an automatic baking process.

In the present embodiment this adverse effect is prevented by hindering the irritating light to pass through an outside window 235. This may be done by tinting or darkening the outside window 235. Then, the irritating light 272 is reflected or absorbed by the outside window 235 and does not reach the inside window 236. Hence, no irritating light 272 is reflected into the camera 260 by the inside window 236 and the camera 260 captures only correct information about the food 280. Therefore, according to the present embodiment a deterioration of the automated food processing procedure is prevented by tinting or darkening the outside window 235.

Thus, to capture images from the heat treatment chamber 120 of the oven 110, it is advantageous to use an illumination apparatus 140 in combination with tinting or darkening of the outside window 235. This provides less impact of outside light to the image processing of the oven inside pictures.

According to the present invention, the visible transmittance of the outside window 135 is lower than the visible transmittance of the inside window 136. Herein, the visible transmittance of the outside window 135 is lower than 95%, more preferably lower than 80%, and in particular lower than 60% of the visible transmittance of the inside window 136. Further, the outside window 235 of the double glass window 130 may have preferably a maximum visible transmittance of 75%. The visible transmittance is the transmittance of light being incident normal to the glass window surface within a visible wavelength range, i.e. between 380 nm to 780 nm.

It is further preferable to tint the window by at least 40%, thus the maximum visible transmittance is 60%. In other words, at least 40% of the incoming light is absorbed or reflected by the outside window 235 and 60% of the light is transmitted through the outside window 235. The inside window 236 may have a visible transmittance of usual glass. It is further preferred to tint the window by at least 60%, leading to a transmittance of 40%. A darkening coating or foil may be applied advantageously at the outside window of a double glass door of the oven to prevent deterioration of the coating due to thermal effects. Due to the darkening of the outside window, reflections of the light coming from an outside of the oven can be significantly reduced. The oven door window can be darkened by a metal foil or coating (mirrored window) or by a tinting foil. The oven door window can be a tinted window comprising e.g. a tinted outside and/or inside glass. If the camera is mounted on the outside window 135, the darkening or reflectivity of the outside window 135 at the location of the camera may be spared, for example by having a hole within the coating to ensure an observation of the camera through the hole in the coating of the outside window 135, wherein the area of the hole is not included for the determination of the transmittance of the outside window 135.

The oven or heat treatment machine 110 may further comprise an oven door or heat treatment machine door, by which the oven chamber 120 can be opened and closed. The oven door may comprise a window, through which the oven chamber 120 can be observed. Preferably, the window comprises the double glass window 130 for preventing thermal loss of the heating energy for the oven chamber 120. Thus, the heat treatment monitoring system 100 may comprise the monitoring apparatus 150 and the oven 110 comprising the monitoring apparatus 150, or an oven 110 having the monitoring apparatus 150 mounted to its oven door.

Thus, also reflections within the double glass window structure of the oven door window can be reduced. Consequently, outside illumination effects on image processing are neglectable. Thus, with a respective illumination intensity of the oven chamber 120, the inside of the oven chamber 120 may be observed by the camera 160 of the monitoring apparatus 150.

Figure 3:
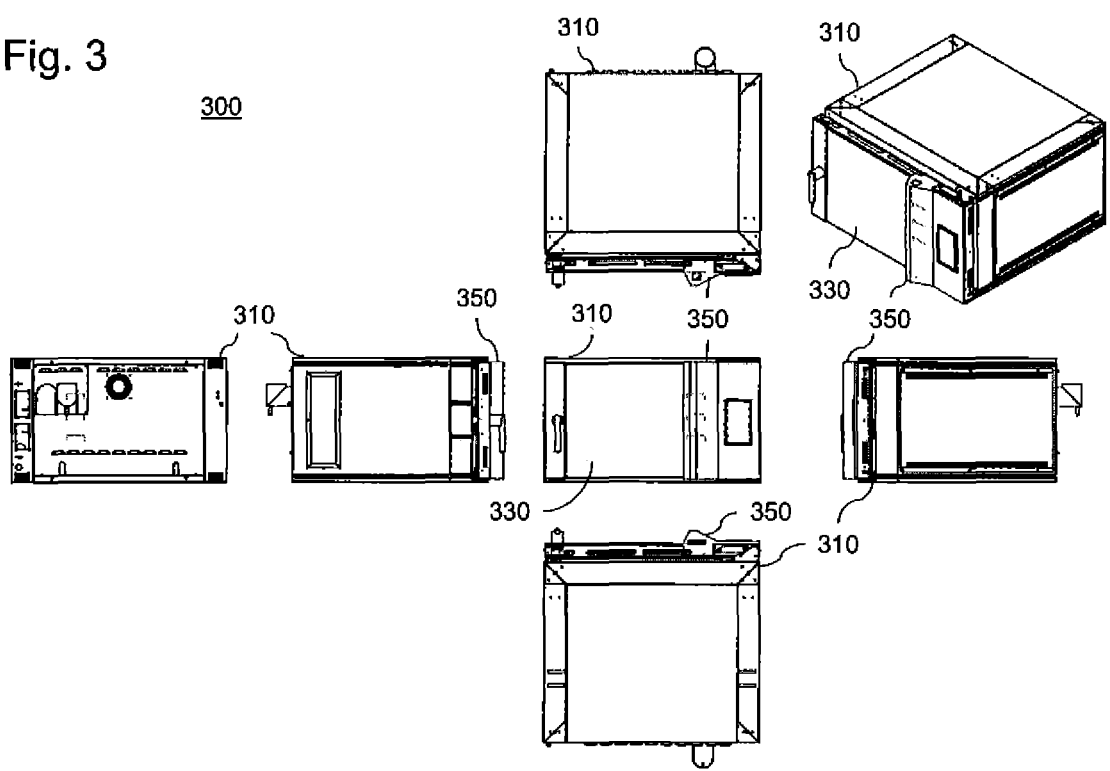
FIG. 3 shows different schematic views of another heat treatment monitoring system.

FIG. 3 shows different views of an embodiment of the heat treatment monitoring system illustrated in FIGS. 1A and 1B.

As illustrated in FIG. 3, a monitoring apparatus 350 is mounted to the front side of an deck oven 310 of a heat treatment monitoring system 300. The monitoring apparatus 350 comprises a casing, a camera sensor mount, and a camera mounted to the camera sensor mount to observe an inside of an oven chamber through an oven door window 330. The camera is tilted in such a way in a horizontal and/or a vertical direction with regard to the oven door window 330 to be adapted to observe at least two baking trays at once in the deck oven 310.

Figure 4:
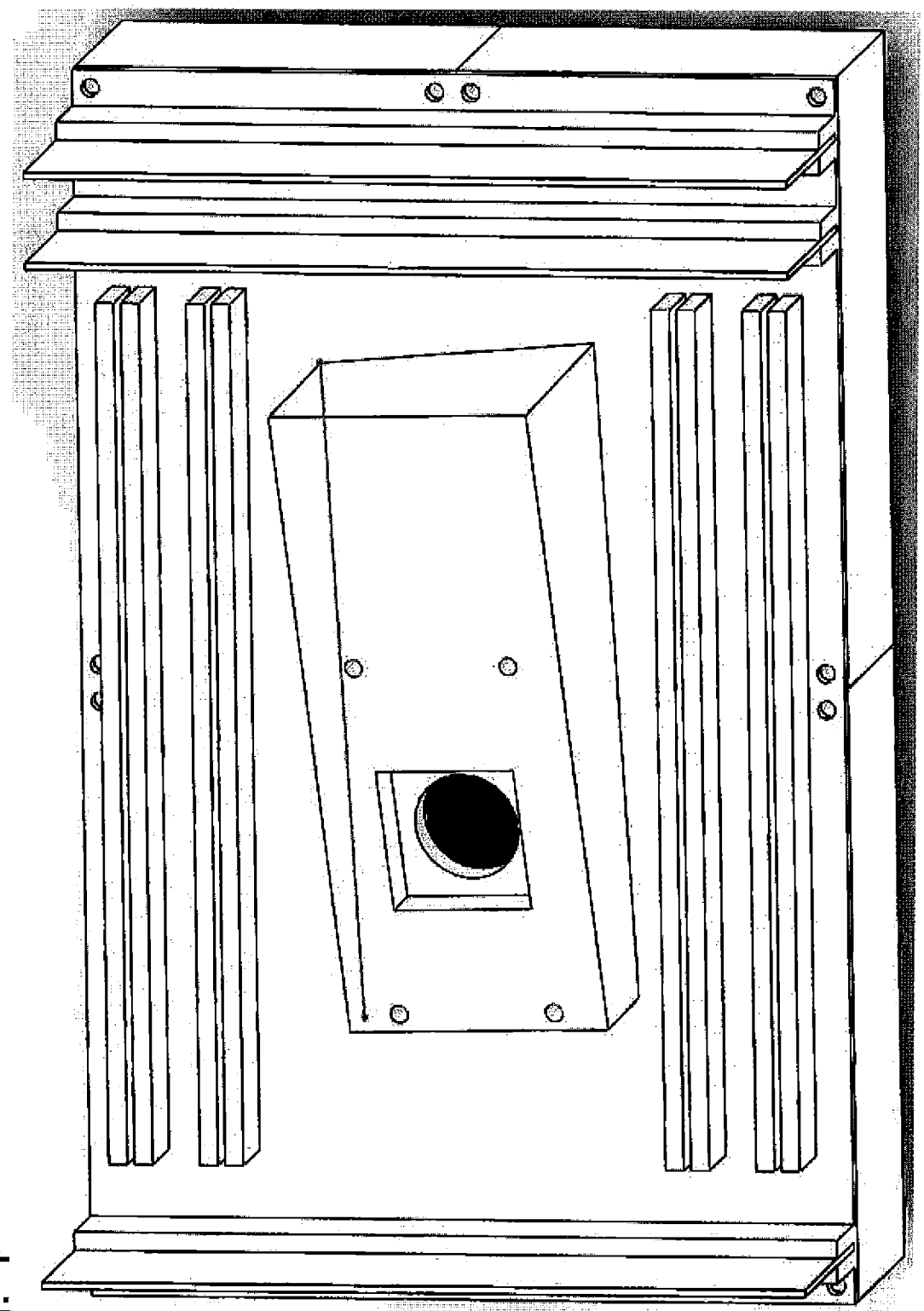
FIG. 4 shows a schematic view of an embodiment of an image sensor.
Figure 5:
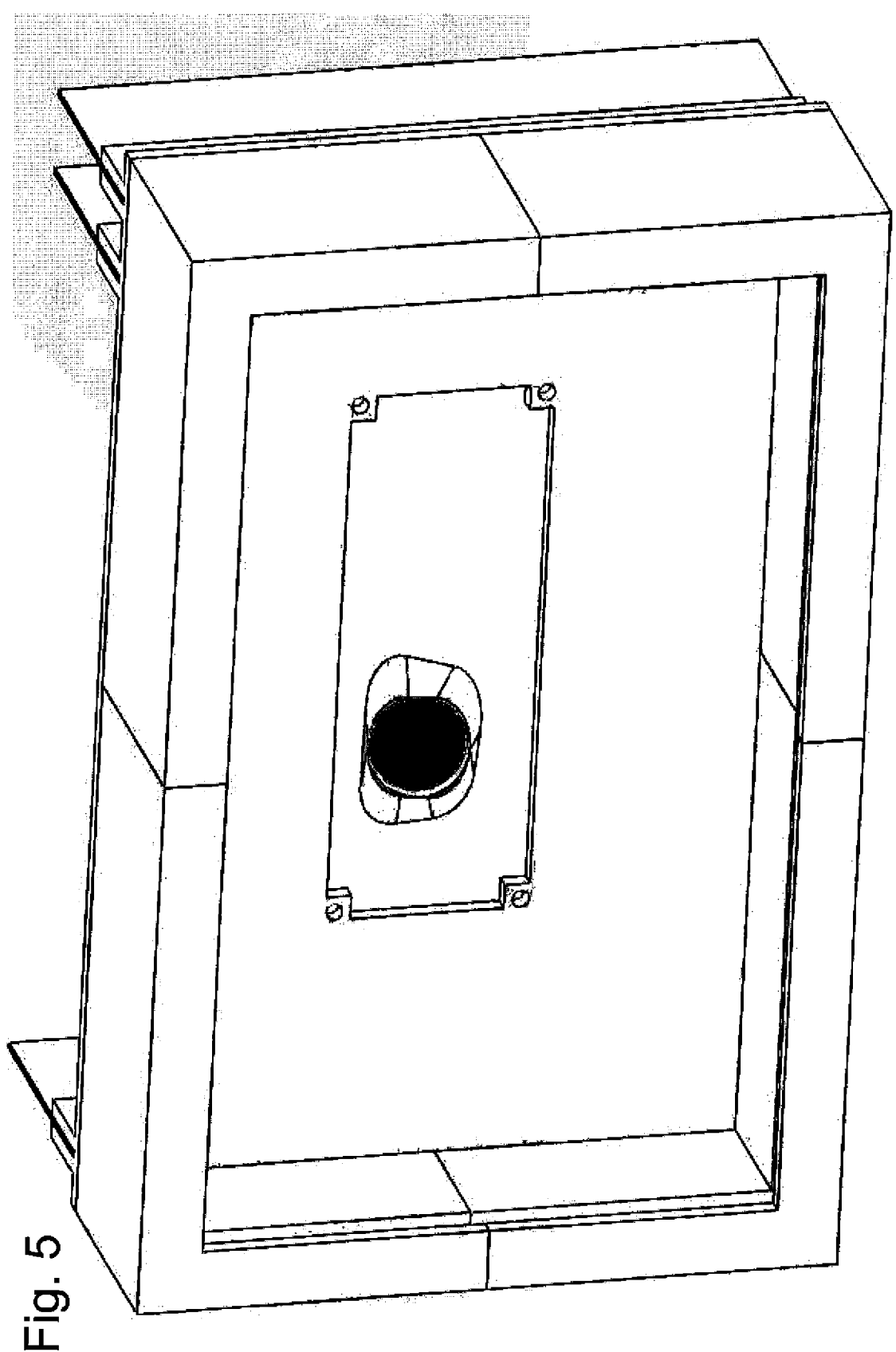
FIG. 5 shows a schematic view of another embodiment of an image sensor.

According to another embodiment the sensor mounting and the casing are cooled with fans for the inside. Further as can be seen from FIGS. 4 and 5 the camera sensor mount of the monitoring apparatus 350 may be equipped with heat sinks and fans to provide cooling. The sensor mount and the casing may be optimized to have an optimal viewing angle to see two baking trays at once in the oven.

Figure 6B:
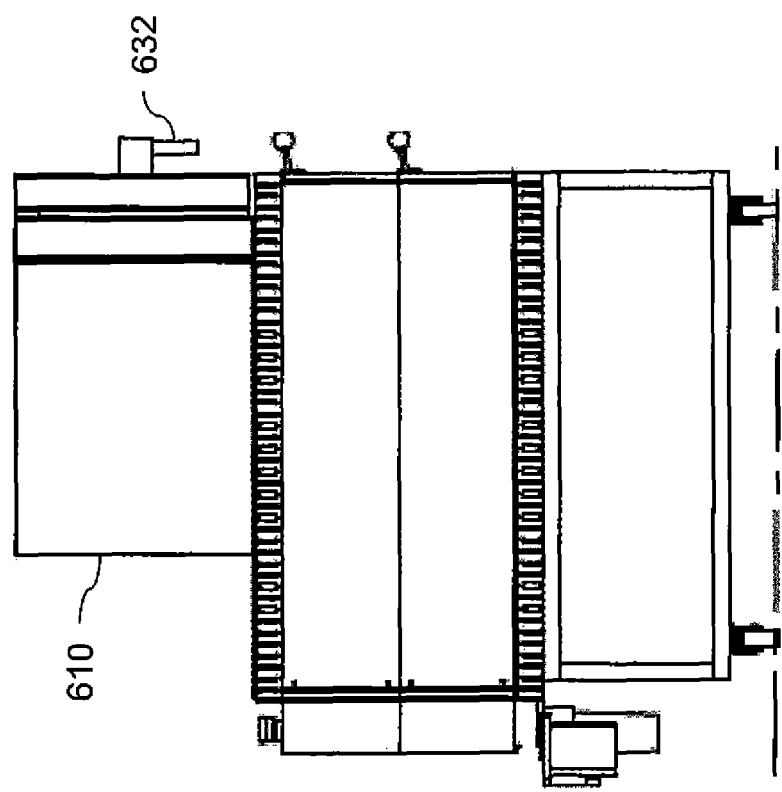
FIGS. 6A and 6B show a schematic front and side view of another embodiment of a heat treatment monitoring system.
Figure 6A:
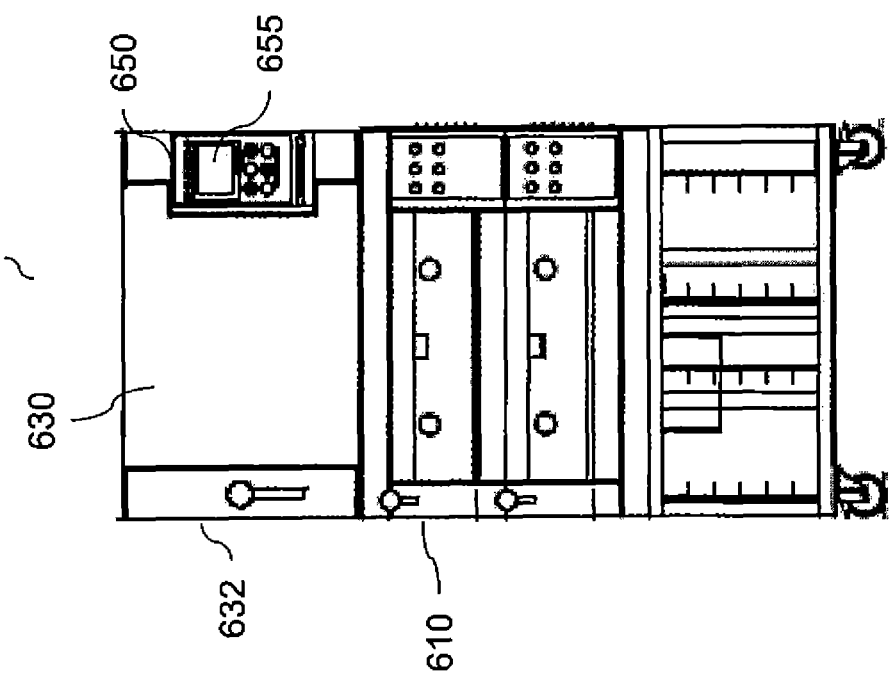

FIGS. 6A and 6B show a top view and a side view of another embodiment of the heat treatment monitoring system illustrated in FIGS. 1A and 1B, respectively.

As illustrated in FIG. 6A a monitoring apparatus 650 is mounted on an oven 610 of a heat treatment monitoring system 600. The monitoring apparatus 650 overlaps partially with a double glass window 630 of an oven door 632. The monitoring apparatus 650 comprises a camera inside a casing. Moreover, the monitoring apparatus 650 comprises a display 655, which allows information to be displayed to a user and enables a user interaction.

The oven 610 may have a convection oven on top and two deck ovens underneath as illustrated in FIGS. 6A and 6B.

Moreover, according to an embodiment the monitoring apparatus 150 may comprise an alert device to inform the user when the baking process has to be ended. In addition, the monitoring apparatus 150 may comprise a control output to stop, for example the heat treatment of the oven 110 and/or to open automatically the oven door and/or to ventilate the oven chamber 120 with cool air or air. The oven 110 and the monitoring apparatus 150 form together the heat treatment monitoring system 100.

According to a further embodiment, the monitoring apparatus 150 is adapted to generate high dynamic range (HDR) processed images of baking goods within the oven chamber 120. This is particularly advantageous in combination with the tinted outside window 135, since the light intensity of the light coming from the baking chamber 120 inside is reduced by the tinting foil and the HDR processing enables better segmentation. Moreover, by using HDR processing a contrast between baking goods and their surroundings like oven walls or trays may be enhanced.

This enables the heat treatment monitoring system 100 to determine a contour or shape of baking goods even more precisely.

FIG. 7 demonstrates a possible sensor setup for a treatment chamber 720 according to a further embodiment. As before, the treatment chamber 720 is monitored with at least one camera 760. The camera 760 may also comprise an image sensor or a photodiode array with at least two photodiodes. It is advantageous to use more than one camera in order to monitor several trays that may be loaded differently. At least one camera 760 may be positioned within the treatment chamber 720 but it is advantageous to apply a window that reduces the heat influence towards the camera(s) 760, in particular a double glass window 730. The double glass window 730 may be in any wall of the treatment chamber.

As described above it is advantageous to apply illumination to the treatment chamber 720 by integrating at least one illumination apparatus as e.g. a bulb or a light-emitting diode (LED). Defined treatment chamber illumination supports taking robust camera images. It is further advantageous to apply illumination for at least one specific wavelength and to apply an appropriate wavelength filter for the camera or image sensor or photodiode array 760. This further increases the robustness of the visual monitoring system. If the wavelength is chosen to be infrared or near-infrared and the image sensor 760 and optional filters are chosen accordingly, the visual monitoring system may gather information related with temperature distribution that may be critical for certain food treatment processes.

The camera or visual system 760 may be equipped with a specific lens system that is optimizing the food visualization. It is not necessary to capture images related to all loaded food, as the processing state of a load is very similar among the load itself. Further it may be equipped with an autofocus system and brightness optimization techniques. It is advantageous to use several image sensors 760 for specific wavelengths in order to gather information about changes in color related to the food treatment. It is advantageous to position the camera or image sensors 760 to gather information of volume change of the food during heat treatment. It may be in particular advantageous to setup a top-view of the food products.

It may also be advantageous to attach a second oven door or treatment chamber opening to a pre-existing opening system. The sensor system or in particular the camera, and the illumination unit may then be position at the height of the oven door window. This door on top of a door or double door system could be applied if the sensor system is retrofitted to an oven.

Each of the monitoring apparatuses described above may be mounted to the front side of an oven, as can be seen for example in FIGS. 1A, 1B, 3, 4A, and 4B. The monitoring apparatus comprises a casing, a camera sensor mount, and a camera mounted to the camera sensor mount to observe an inside of an oven chamber through an oven door window. The camera is tilted in such a way in a horizontal and/or a vertical direction with regard to the oven door window to be adapted to observe at least two baking trays at once in the deck oven. The monitoring apparatus may further comprise an alert device to inform the user when the baking process has to be ended. In addition, the monitoring apparatus may comprise a control output to stop, for example the heating of the oven and/or to open automatically the oven door and/or to ventilate the oven chamber with cool air or air. The oven and the monitoring apparatus form together a heat treatment monitoring system.

As discussed above one camera sensor is used to observe the baking processes. According to another embodiment it is beneficial to use several camera sensors. If every tray within a heat treatment chamber has at least one camera sensor aligned, a monitoring and control software may gain information for every tray individually. Thus, it is possible to calculate a remaining baking time for every tray.

The remaining baking time may be used to alert the oven user to open the door and take out at least one of the trays, if the baking time has ended before the other trays. According to the invention it is possible to alert the user by means of a remote or information technology system. The alert may happen on a website display, on a smart phone, or on a flashlight next to the counter. This has the advantage that the user is being alerted at their usual working place that may be not in front of the oven.

According to another embodiment of the monitoring system of the present invention the monitoring system may be used in industrial food production systems, e.g. in baking or pre-baking lines or in dough preparation systems that form and portion dough. However, the monitoring system may also be used in any other area of food production or processing.

FIG. 8 illustrates a monitoring system 800 with at least one sensor system setup 850, for heat treatment machines or ovens 810 (baking units) with belt conveyor 815 (moving unit). These ovens 810 are usually used in industrial food production systems.

The sensor system 850 may have at least one sensor of the following: hygrometer, insertion temperature sensor, treatment chamber temperature sensor, acoustic sensors, laser triangulation, scales, timer, camera, image sensor, array of photodiodes. Part of this sensor system 850 is also the supporting devices such as illumination or cooling or movement algorithms.

According to an embodiment laser triangulation may be used to acquire information regarding a food volume. Then the sensor system setup 850 comprises a laser light distribution unit, which generates and directs laser beams towards baking goods within the oven or baking unit 810. The laser light distribution unit may direct the laser beams on a single piece of baking good at the same time or, according to another embodiment at least twice within the food treatment process to acquire information regarding the change of volume over time.

The volume information and/or a height profile of the baking good is then acquired by a measuring unit, which analyses detection results of light detection units, which detect the reflection of the laser beams from the baking goods. There may be a single or several light detection units for all laser beams or one light detection unit for each laser beam.

According to another embodiment at least one additional sensor system 852 may be placed at different positions inside or outside of the heat treatment machine. Alternatively, the sensor system 850 may be applied at a position where the belt conveyor passes the food twice at different times of processing. Alternatively, the sensor system 850 may move with the same speed as the belt conveyor 815.

Figure 9:
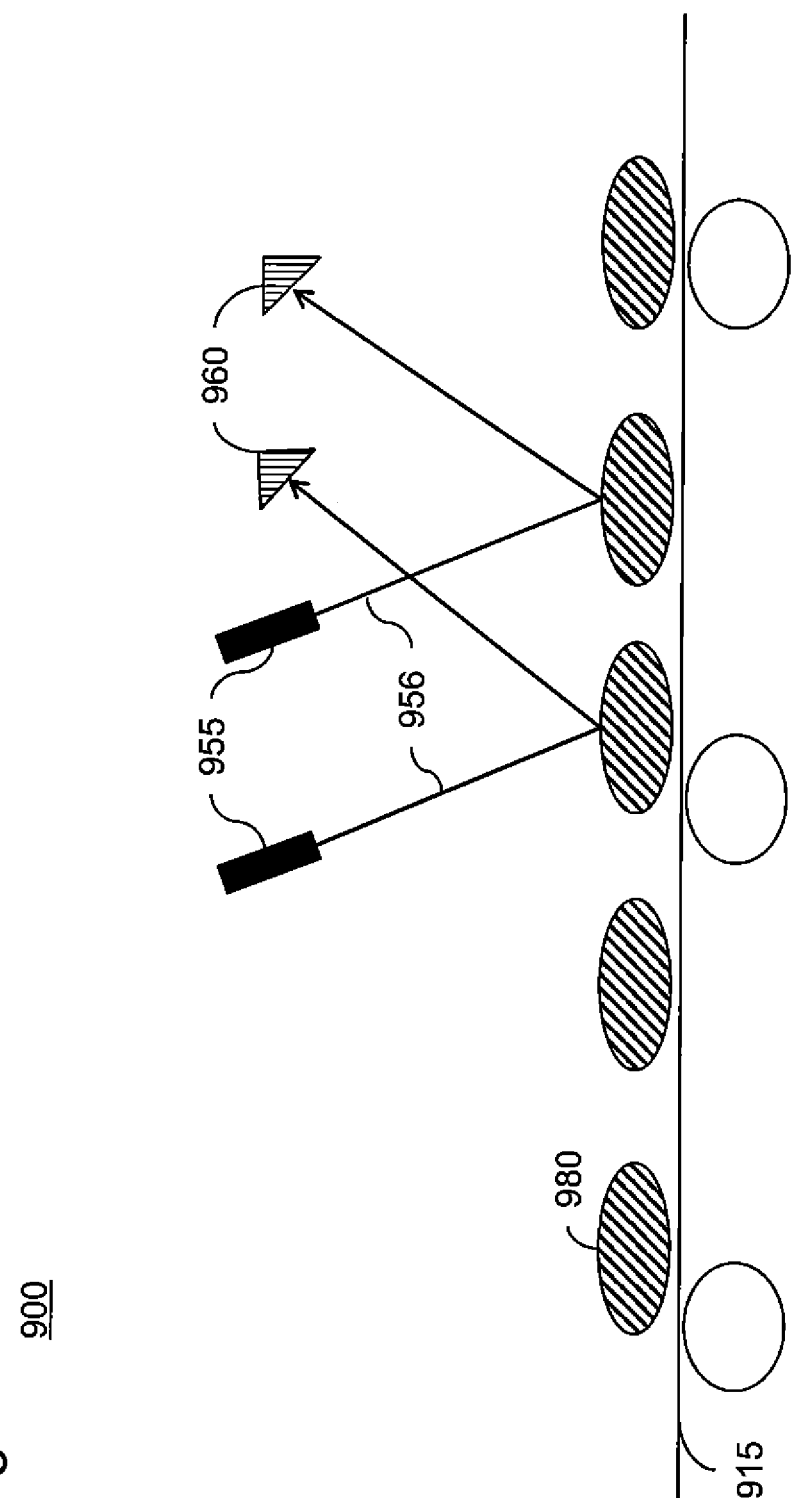
FIG. 9 shows a schematic view of an embodiment of a food production system using laser triangulation.

According to further embodiments more than one camera sensor or optical sensor and more than one laser line generator for laser triangulation may be used. According to an embodiment illustrated in. FIG. 9, a monitoring system 900 comprises at least two monitoring apparatuses each with a laser line generator 955 and a light receiving device 960 as e.g. a camera or a photo diode array. Thus, a laser light distribution unit according to this embodiment comprises a first laser light generating unit and a second laser light generating unit.

From the laser light generators 955 laser beams 956 are emitted towards food 980 as e.g. raw or pre-baked dough on a belt conveyor 915. From the food 980 the laser beams are reflected towards the light receiving devices 960. As the position of the laser light generators 955 and the light receiving devices 960 with respect to each other and with respect to the belt conveyor 915 is known, the distance of the laser light generators 955 to the food 980 can be obtained by triangulation from the exact position at which the laser beams 956 are observed within the light receiving devices 960. Hence, using such laser triangulation the surface profile of processed food 980 may be determined.

As is shown in FIG. 9 the laser beams 956 are directed directly towards the food or baking goods 980 and are scattered directly towards the light receiving devices or light detection units 960. According to another embodiment the light paths of the laser beams may be altered by deflection or guiding mirrors. Then, the laser light generators 955 or the light detection units 960 may be located also outside of the heat treatment chamber or baking unit. This allows for a more flexible design of the heat treatment monitoring system. Moreover, in order to prevent steaming up of the mirrors, these may be heated to a temperature sufficiently high to hinder the steaming up, but low enough to not damage the mirrors.

As shown in FIG. 9 the laser beams 956 from the laser light generators 955 are focused such that food 980 at different stages of production is monitored. Note that although in FIG. 9 it is shown that the laser light generators 955 focus on two neighboring pieces of food 980, they may just as well focus on pieces of food 980 which are a greater distance apart from each other. For example, the two pieces of food may be separated by several meters or the laser light generators 955 may be located at an entrance and the exit of a baking chamber through which the belt conveyor 915 runs and observe the surface profile of food 980 during entry and exit of the baking chamber. To this end, the laser light generators or generation units 955 may also be arranged such that they emit light nearly perpendicular from the top towards the food 980.

Note also that the laser line generators 955 do not need to be located above the belt conveyor 915, but may also be located at a side of the belt conveyor 915. Of course the at least two laser line generators 955 may also be located at different sides of the belt conveyor 915.

Hence, by using two or more laser light generators 955 that focus on different pieces of food 980 and observe the respective surface structure of the pieces of food 980 a difference in this surface structure caused by the baking or food production process may be observed, as the belt conveyor or moving unit 915 moves food 980 through the baking unit from a focus point of a first laser beam towards a focus point of a second laser beam. This information about the difference in surface structure at various stages of the baking or food production process may be used to automatically control the process and hence allows for automated baking or food production.

The laser beams 956 may be dot-like or may be fan-shaped and extend across the whole width of the belt of the belt conveyor 915. By using fan-shaped laser beams 956 a three dimensional profile of the food 980 running on the belt conveyor 915 may be obtained that may serve even better for automatically controlling the baking or food production process. Then, the reflection of the fan shaped laser beams from the food may be collimated or concentrated by lenses on the light detection units 960, in order to allow for small light detection units 960 which can be easily integrated in the heat treatment monitoring system.

Figure 10:
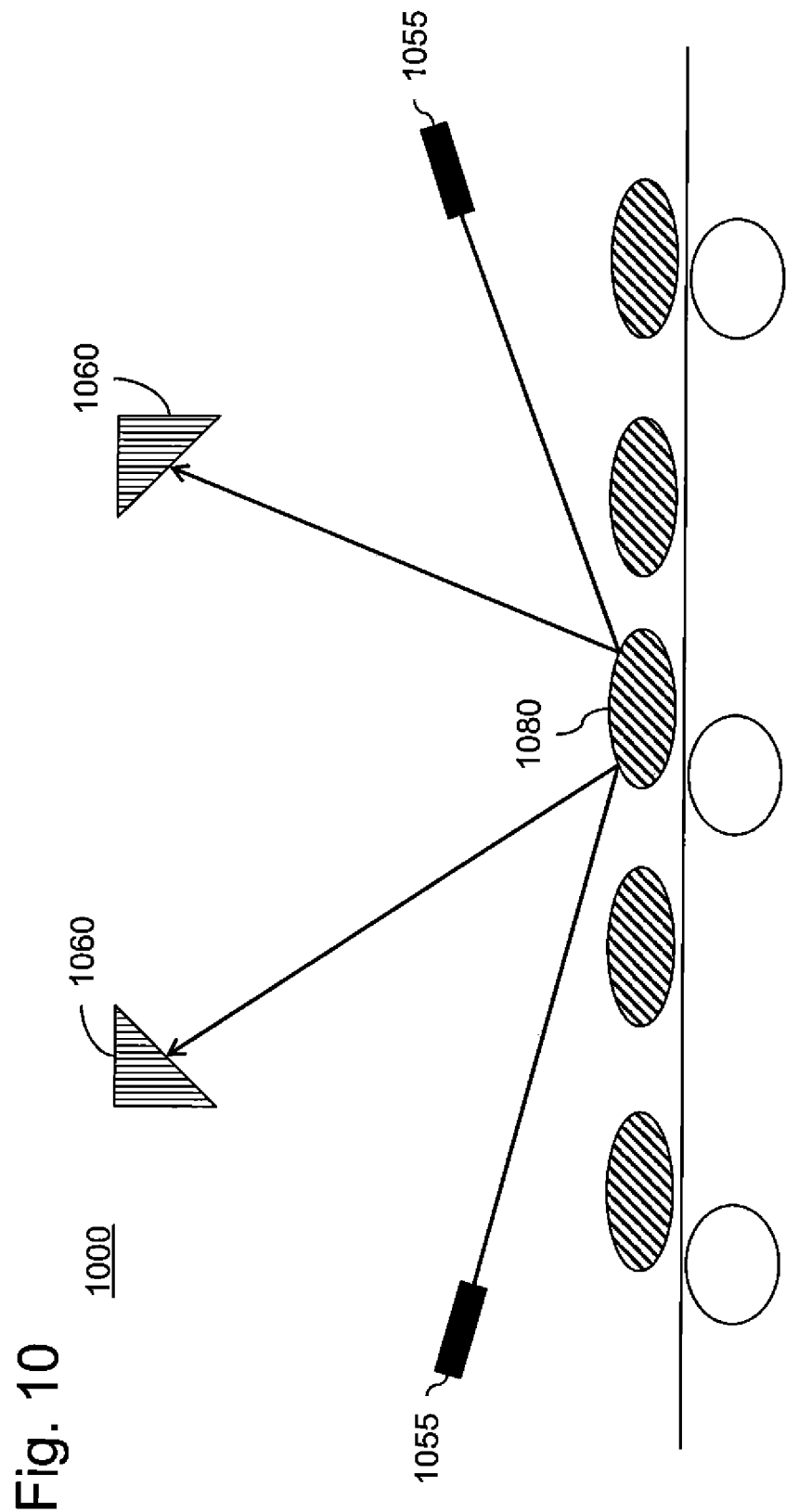
FIG. 10 shows a schematic view of another embodiment of a food production system using laser triangulation.

As shown in FIG. 10 in addition to observing different pieces of food it is especially beneficial to align at least two sensor systems of a monitoring system 1000 per piece of food in a 45 degree tilted angle, observing the measurement objects 1080 from top left and top right. This is advantageous because when observing round objects, laser light generators 1055 and their respectively aligned light receiving devices 1060 can measure the surface structure of the round objects in areas, that may have been obscured when only using one sensor from a top view would have been used. According to another embodiment the laser beams may be inclined even less than 45° with respect to the conveyor belt or the tray, which supports the food 1080. Then, the surface structure near the support of the food may be observed even better.

In case that fan shaped laser beams are used, the inclination of the planes spanned by the fans should be less than 45° with respect to the support of the food 1080. This also means that the angle between the laser beams has to be greater than 90°.

Note that although in FIG. 10 it is shown that the laser light generators 1055 focus on the same piece of food 1080, they may just as well focus on two different pieces of food 1080, which are separated from each other. For example, the two pieces of food may be separated by several meters or the laser light generators 1055 may be located at an entrance and the exit of a baking chamber through which the belt conveyor runs and observe the surface profile of food 1080 during entry and exit of the baking chamber.

Note also that the laser line generators 1055 do not need to be located above the belt conveyor, but may also be located at a side of the belt conveyor. Of course the at laser line generators 1055 may also be located at different sides of the belt conveyor.

Furthermore according to another embodiment there may be a laser triangulation display within the oven. Then, at least two laser triangulation sensors and two line lasers, looking at the baked products from approximately 45 degree angle (top left and top right) may be used. This gives the advantage that one can measure also the rounding of the baked products at their bottom, while by using one laser line and camera from top view, the bottom half rounding is obscured and not accounted for in the measurements.

Hence, according to these embodiments additional information about the baking or food production process may be provided based on which automated baking or food production may be performed more efficient and reliable.

According to another embodiment a laser line generator, or any other light source, and a camera sensor, or any other optical sensor, may be used to grasp information about the food being processed. With the procedure described above, also known as laser triangulation, a laser line may be projected onto a measurement object. An optical sensor, a sensor array or typically a camera can be directed towards this measurement object. If the camera perspective or the viewing point and the respective plane and the plane of the laser line generator, formed by the light source and the ends of the projected laser line, are not parallel or are at an angle, the detected optical information may be used to perform measurements providing information about size and shapes including a three dimensional structure or volume. In the embodiments described above two laser light generating units have been used in order to generate and direct the laser beams. According to another embodiment a primary laser light generating unit may be used to generate a primary laser beam, which is then distributed by an optical unit within the baking unit. Using such structure within the heat treatment monitoring system makes it possible to save energy costs and space by reducing the number of laser light generating units.

Moreover, the laser light generating unit may be located outside of the baking unit and only the primary laser beam may be input into the baking unit. This makes it possible to choose a structure of the heat treatment monitoring system more flexibly, especially if also the light detection units are provided outside of the baking unit.

The optical unit may be any type of optical system that allows for splitting of a single primary laser beam into two or more laser beams. For example, the optical system may comprise a semi-transparent mirror, which reflects a part of the primary laser beam towards a first position to be observed and transmits a part of the primary laser beam toward a mirror, which reflects the light towards a second position of interest. The primary laser beam may also be separated such that its parts are directly directed towards the positions to be observed. According to another embodiment there may also be more mirrors and/or lenses within the light path of the primary laser beam.

According to another embodiment the optical unit may comprise a movable and rotatable mirror, which generates laser beams alternately. To this end the moveable and rotatable mirror may be provided above the food or baking goods and may be moved and rotated such that the primary laser beam is directed to different pieces of food or different positions on a single piece of food at different times. Hence, volume information collected by the measurement unit will refer to different positions within the baking unit according to time.

Using such mirrors reduces the space requirements within the baking unit and allows for a flexible design of the heat treatment monitoring system. Moreover, a user may switch operation easily from a mode, in which two different pieces of food are observed, in order to obtain information about the change of the height profile and/or volume profile of the food, and a mode, in which a single piece of food is observed from different directions, in order to obtain the overall three-dimensional shape of the piece of food also near the support of the piece of food. The movable and rotatable mirror may also perform such different tasks in parallel.

Of course also the mirrors used in connection with a primary laser beam may be heated in order to prevent steam up.

According to another embodiment, the optical system constituted by the laser light distribution unit, the food or baking good, and the light detection unit may satisfy the Scheimpflug principle. This guarantees that the image of the baking good sampled by the laser beams is always focused on the light detection unit, and allows therefore for an exact measurement of a height profile of the baking good.

According to another embodiment laser triangulation may be combined with grey image processing to gather simultaneous information about shape and size as well as information about texture, colour and other optical features. The resulting process data may be used to generate unique features for the measurement object, in this case food. This may be shape, size, volume, colour, browning, texture, pore size and density of food being processed such as dough or baked bread, which may be sliced. Some or all of the named information may be used to interpret the sensor data, in order to allow for automated baking or food processing In the embodiments described above the data capturing is performed mainly by image sensors such as cameras or photo diode arrays. However, according to further embodiments the data obtained by the image sensors may be supplemented with data from a variety of other sensors such as e.g. hygrometers, insertion temperature sensors, treatment chamber temperature sensors, acoustic sensors, laser, scales, and timers. Furthermore, a gas analyser of the gas inside the treatment chamber, means for determining temperature profiles of insertion temperature sensors, means for determining electromagnetic or acoustic process emissions of the food to be treated like light or sound being reflected or emitted in response to light or sound sources, means for determining results from 3D measurements of the food to be heated including 3D or stereo camera systems or radar, means for determining the type or constitution or pattern or optical characteristics or volume or the mass of the food to be treated can be also used as sensors for the sensor unit 1810 as described below. Automated food processing or baking may then be controlled based on all data from all sensors.

For example, referring back to FIG. 7, the treatment chamber 720 may be further equipped with at least one temperature sensor or thermometer 762. Although this is only illustrated within FIG. 7 any other embodiment described herein may also comprise such a temperature sensor 762. When treating food with heat, temperature information relates to process characteristics. It may contain information towards heat development over time and its distribution inside the treatment chamber. It may also gather information about the state of the oven, its heat treatment system and optional pre-heating.

It may also be advantageous to integrate insertion thermometers. Insertion thermometers enable to gather inside food temperature information that is critical to determine the food processing state. It is advantageous in bread baking to acquire information related to the inside and crumb temperature.

Moreover, a color change progress in time of the food to be heated may be used to determine an actual temperature within the oven chamber and may be further used for a respective temperature control in the baking process. The treatment chamber 720 or any other embodiment described herein may be equipped with at least one sensor related to treatment chamber humidity such as a hygrometer 764. In particular for bread baking gathering information related to humidity is advantageous. When the dough is heated the containing water evaporates resulting in a difference in inside treatment chamber humidity. For instance, with air circulation the treatment chamber humidity during a baking process may first rise and then fall indicating the food processing state.

The treatment chamber 720 or any other embodiment described herein may further be equipped with at least one sensor gathering information of the loaded food weight and eventually its distribution. This may be accomplished by integrating scales 766 in a tray mounting system of the heat treatment chamber 720. The tray mounting or stack mounting may be supported by rotatable wheels or discs easing the loading of the oven. The scales 766 could be integrated with the wheels or discs and take them as transducer. It is advantageous to acquire the weight information for every used tray or set of trays individually in order to have information related about the total food weight and its relative distribution as the desired energy supply and its direction during the heat treatment may vary significantly. Further it is advantageous to acquire information of the food weight differences over time while treating it with heat. For instance in bread baking, the dough roughly loses around 10% of its initial weight. Further, it is possible to acquire information regarding the state of dough or food by emission and capturing of sound signals, e.g. by a loudspeaker and microphone 768.

Moreover, in the described embodiments alternative cameras or image sensors or photodiode array sensors and eventually alternative illumination setups may be used. Instead of placing the camera behind a window on any treatment chamber wall, it or a second camera may as well be integrated with the oven door or treatment chamber opening.

Instead of integrating illumination into any treatment chamber wall, it may as well be integrated into the oven door or treatment chamber opening. Commonly ovens door have windows to enable human operators to visually see the food treated and to supervise the process. According to another embodiment at least one camera or image sensor or photodiode array or any other imaging device may be integrated into an oven door or a treatment chamber opening. An oven door without window for human operators may be designed more energy efficient as heat isolation may be better. Further, differences in outside lightening do not influence with the treatment chamber monitoring camera images that would then only rely on the defined treatment chamber illumination. However, one should note that such a setup might not be easily installed later on an already existing oven.

Further, it may be advantageous to integrate a screen or digital visual display on the outside wall of the oven door or at any other place outside of the treatment chamber. This screen may show images captured from the treatment chamber monitoring camera. This enables a human operator to visually supervise the baking process, although it is an object of the invention to make this unnecessary.

Figure 11:
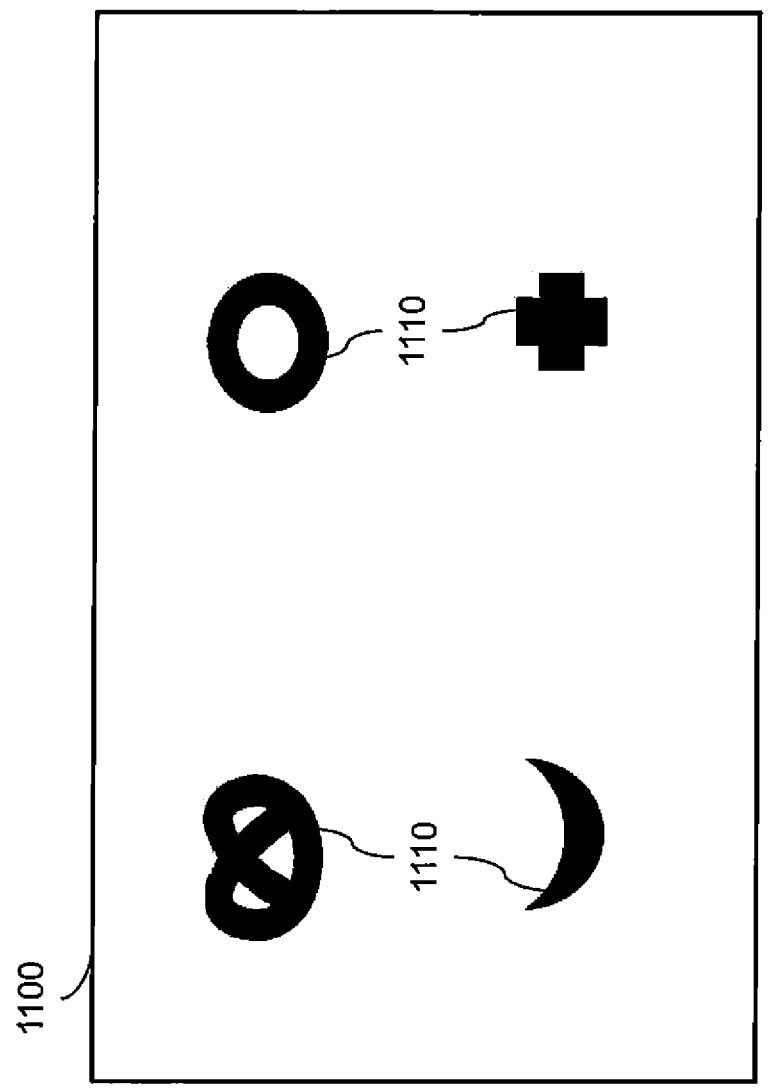
FIG. 11 shows a schematic top view of an embodiment of a tray with indication for arranging dough.

Further, it may be advantageous to use trays or a stack of trays that indicates the food distribution. For instance, in bread baking, when loading the oven the dough placement may vary for every baking cycle. These differences can be coped with by image processing with matching and recognition techniques. It is advantageous to have a similar loading or food placement for every production cycle as indicated in FIG. 11. An automated placement system may be applied when setting trays 1100. For manual placements at least some of the used trays may have indication 1110 of where to place the dough. As indication bumps, dumps, pans, molds, food icons, food drawings, or lines may be used.

Moreover, when integrating a camera sensor in an oven environment or a food processing system it may be of advantage to integrate cooling devices. These may be at least one cooling plate, at least one fan and/or at least one water cooling system.

Further, a shutter may be used, that only exposes the camera sensor when necessary. It may often not be necessary to take many pictures and it may often be feasible to only take pictures every 5 seconds or less. If the shutter only opens every 5 seconds the heat impact on the camera chip is significantly lower, which reduces the possibility of an error due to a heat impact and thus increases the reliability of the heat treatment monitoring system.

It may be further of advantage to take at least two pictures or more or take one exposure with several non-destructive read outs and combine the pixel values. Combining may be to take a mean or to calculate one picture out of at least two by means of High Dynamic Range Imaging. In combination with a shutter or stand alone it is possible to apply wavelength filters, that let only relevant wavelengths pass, for instance visible light or infrared radiation. This may further reduce the heat impact on the camera chip and hence increase the reliability of the monitoring system even further.

Figure 12:
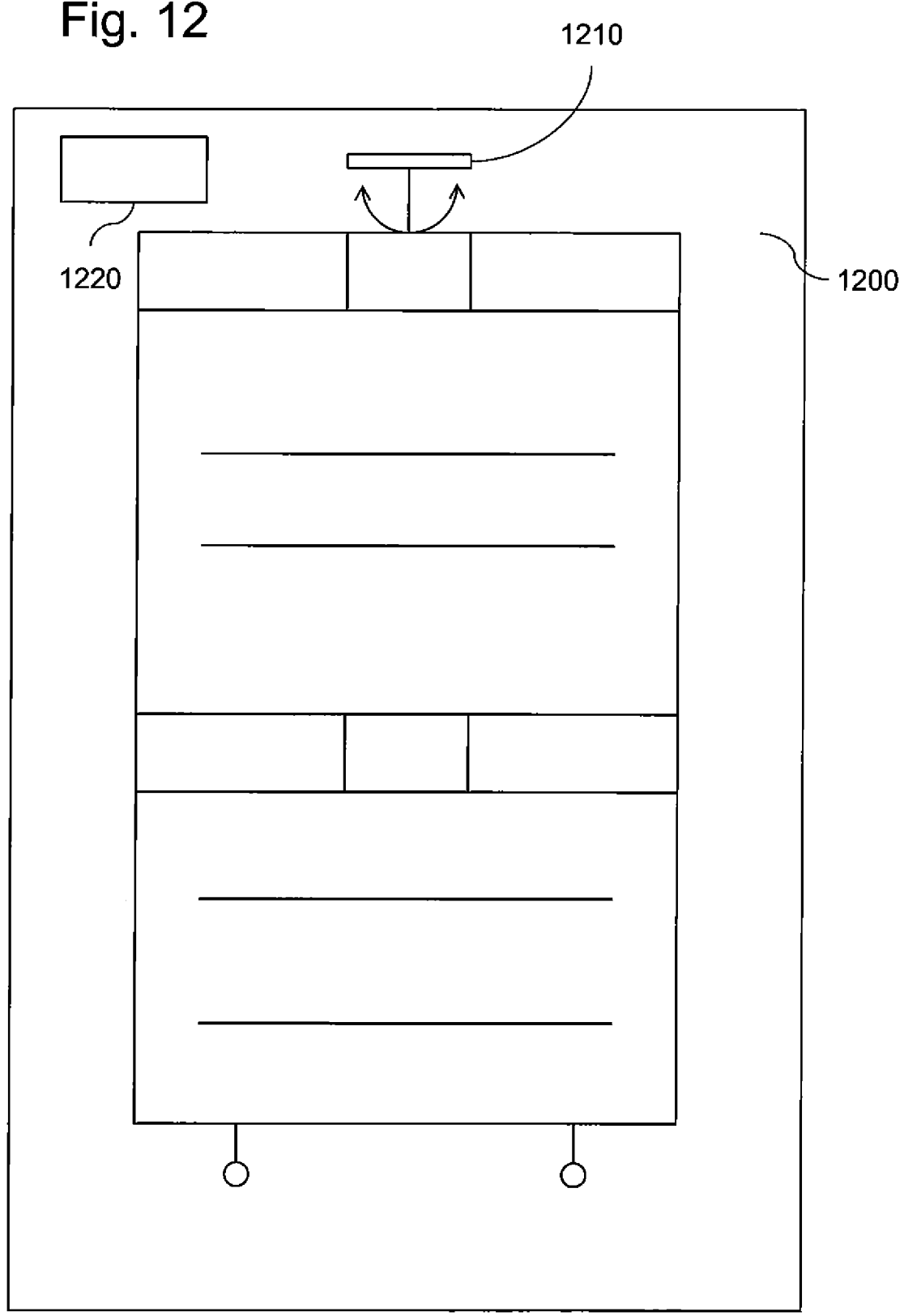
FIG. 12 shows a schematic view of an embodiment of a sensor system integrated in an oven rack.

In another embodiment, illustrated in FIG. 12, a sensor system integration for oven racks or moving carts used in some oven designs may be used. For rotating rack ovens, the sensor system may be integrated into the oven rack as demonstrated with 1200. The sensor system is integrated above at least one of the food carrying trays. The sensor system in the cart may have at least one sensor of the following: hygrometer, insertion temperature sensor, treatment chamber temperature sensor, acoustic sensors, scales, timer, camera, image sensor, array of photodiodes. Part of the rack integrated sensor system is also supporting devices such as illumination or cooling as demonstrated in this invention. It further is object of the invention to have an electrical connection such as a wire or electrical plugs at the mounting of the rack as demonstrated with 1210. It is further advantageous to integrate at least part of the sensor system into the rotating rack oven wall as demonstrated with 1220. This is advantageous to reduce the heat effects onto the sensor system. For the camera, image sensor, or photodiode array it is advantageous to apply an image rotation or movement correction algorithm in order to correct the rack rotation or food movement. This algorithm may be supported by a measured or pre-set parameter from the oven control regarding the rotation or movement speed.

In another embodiment a graphical user interface (GUI) may show pictures of every tray and deck within an oven. In a convection oven the end time for every tray may be determined separately. This means that if one tray is finished earlier than another, the user may get a signal to empty this tray and leave the others in. This is advantageous because many ovens may not have equal results for different trays. Moreover, one may bake different products on each tray, if they have approximately the same baking temperature. Hence, it is possible to operate a single oven more flexible and efficient.

In another embodiment the oven may also determines the distribution of the baked goods on a tray. An oven may also reject poorly loaded trays.

Using one or several of the sensors described above data about the baking or food processing procedure may be collected. In order to allow for an efficient and reliable automated baking or food processing the processing machines such as ovens or belt conveyors need to learn how to extract relevant data from all data, how to classify the processed food and the stage of food processing based on these data, and how to automatically control the processing based on the data and the classification. This may be achieved by a heat treatment monitoring system that is able to control a baking process based on machine learning techniques.

Figure 13:
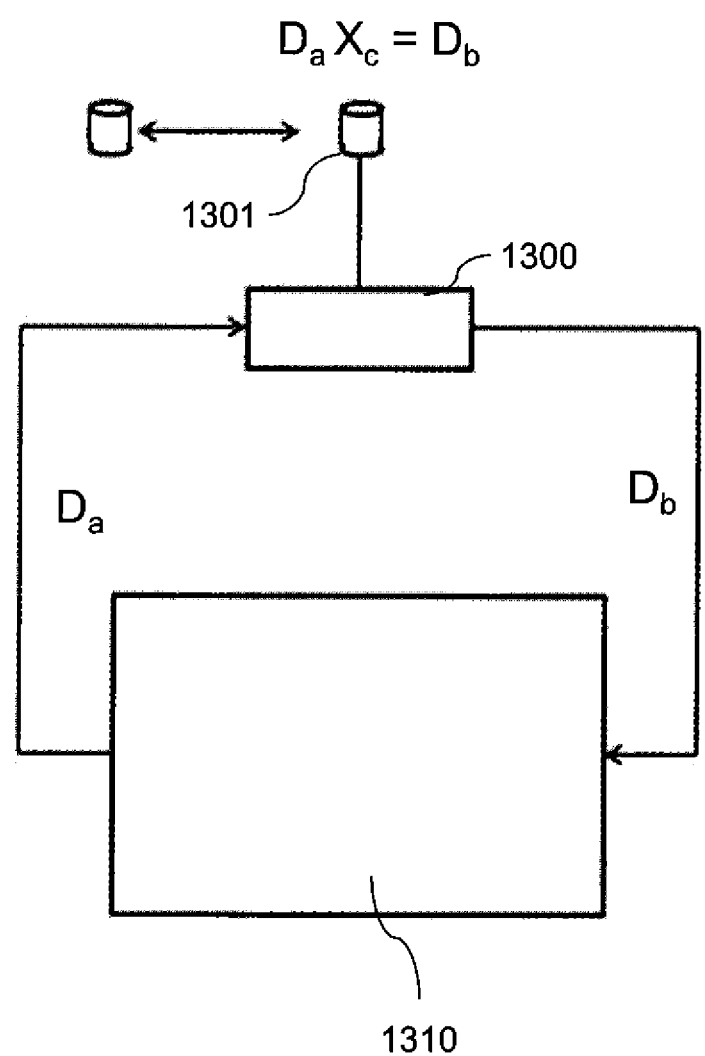
FIG. 13 shows a schematic data processing flow of an embodiment of a heat treatment monitoring system.

FIG. 13 demonstrates a control unit and a data processing diagram according to which the data of any of the aforementioned embodiments may be handled.

Here, the control unit or heat treatment monitoring system 1300, for the heat treatment machine 1310, recognizes the food to be processed with any of the described sensor systems. The recognition of the food to be processed may be accomplished with the unique sensor data input matrix $D_a$.

This sensor data input matrix or a reduced representation of it can be used to identify a food treatment process with its data characteristic or data fingerprint.

The control unit 1300 has access to a database that enables to compare the sensor data input matrix with previously stored information, indicated with 1301. This enables the control unit 1300 to choose a control program or processing procedure for the present food treatment. Part of this procedure is according to an embodiment a mapping $X_c$ of the sensor data input matrix $D_a$ to an actuator control data matrix $D_b$, $$D_a X_c = D_b. \quad \text{(Formula 1.00)}$$

With the actuator control data matrix $D_b$ the heat treatment machine 1310 controls the food processing, for instance by controlling oven control parameters such as energy supply or start and end time of processing. The heat treatment machine then operates in a closed-loop control mode. Typically, the sensor data input matrix $D_a$ is significantly higher in dimension compared to the actuator control data matrix $D_b$.

According to an embodiment it is advantageous to find a mapping $X_c$ as well as a reduced representation of the sensor data input matrix $D_a$ with methods known from machine learning. This is because the type of food to be processed and the according procedures are usually individually different.

From a data processing point of view the relations between sensor data input and appropriate actuator output may be highly non-linear and time dependent. Today these parameters are chosen by human operators commonly with significant know how in a time consuming configuration of the heat treatment machine. According to an embodiment of the present invention with initial data sets learned from a human operator, machine learning methods can perform the future system configuration and expedite configuration times as well as increase processing efficiency as well as quality.

All applied data may be stored in databases. According to the invention it is beneficial to connect the heat treatment machine with a network. With the means of this network, any database data may be exchanged. This enables a human operator to interact with several locally distributed heat treatment machines. In order to do so the heat treatment machine has equipment to interact with a network and use certain protocols such as Transmission Control Protocol (TCP) and Internet Protocol (IP). According to the invention the heat treatment machine can be equipped with network devices for a local area network (LAN) a wireless area network (WLAN) or a mobile network access used in mobile telecommunication.

In any of the previously described embodiment a baking or food processing procedure may contain a learning phase and a production phase. In the learning phase a human operator puts food into the heat treatment machine. It is treated with heat as desired by the human operator. This can be carried out with and without pre-heating of the heat treatment chamber. After the processing with heat the human operator may specify the type of food and when the desired process state has been reached. The human operator can also provide information when the product was under baked, over baked and at desired process state.

Using the described machine learning methods the machine calculates the processing parameters for future food production. Then the heat treatment machine or heat treatment machines in a connected network can be used to have additional learning phases or go into automated production.

When in automated production the human operator just puts the food into the heat treatment machine with optional pre-heating. The machine then detects the food in the treatment chamber and performs the previously learned heat treatment procedure.

When the desired food process state has been reached or simply, when the bread is done, the machine ends the heat treatment process. It can do so by opening the door or end the energy supply or ventilate the hot air out of the treatment chamber. It can also give the human operator a visual or acoustical signal. Further, the heat treatment machine may ask for feedback from the human operator. It may ask to pick a category such as under baked, good, or over baked. An automated loading system that loads and unloads the treatment chamber may fully automate the procedure. For this purpose a robotic arm or a convection belt may be used.

Recent techniques in machine learning and the control of food processing have been examined to create adaptive monitoring. Artificial Neural Networks (ANN), Support Vector Machines (SVM), and the Fuzzy K-Nearest Neighbor (KNN) classification have been investigated as they apply to special applications for food processing. One aim of the present invention is to evaluate what machine learning can accomplish without a process model defined by a human operator.

In the following, a brief overview of the theories underlying the present invention is given. This includes techniques for reducing sensor data with dimensionality reduction, such as Principal Component Analysis, Linear Discriminant Analysis, and Isometric Feature Mapping. It also includes an introduction of classification and supervised as well as unsupervised learning methods such as Fuzzy K-Nearest Neighbor, Artificial Neural Networks, Support Vector Machines, and reinforcement learning. For the number format, the thousand separator is a comma ",", and the decimal separator is a point "."; thus, one-thousand is represented by the number 1,000.00.

Feature Extraction and Dimensionality Reduction

Figure 14:
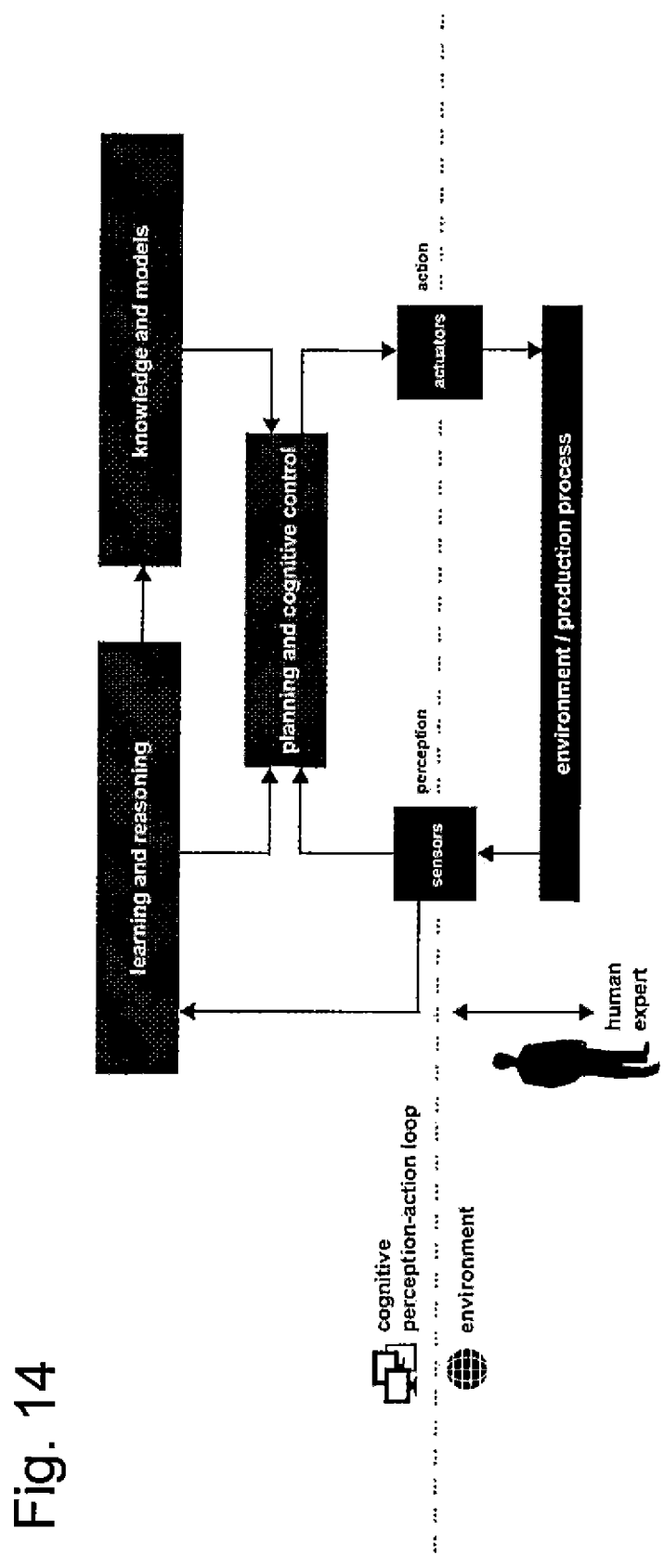
FIG. 14 shows a cognitive perception-action loop for food production machines with sensors and actuators according to the present invention.

The present invention does not seek nor desire to achieve human-like behavior in machines. However, the investigation of something like cognitive capabilities within food processing or production machines of artificial agents capable of managing food processing tasks may provide an application scenario for some of the most sophisticated approaches towards cognitive architectures. Approaches for production machines may be structured within a cognitive perception-action loop architecture, as shown in FIG. 14, which also defines cognitive technical systems. Cognitive capabilities such as perception, learning, and gaining knowledge allow a machine to interact with an environment autonomously through sensors and actuators. Therefore, in the following, some methods known from machine learning that will be suitable for different parts of a cognitive perception-action loop working in a production system will be discussed.

If a cognitive technical system simply has a feature representation of its sensor data input, it may be able to handle a higher volume of data. Moreover, extracting features emphasizes or increases the signal-to-noise ratio by focusing on the more relevant information of a data set. However, there are many ways of extracting relevant features from a data set, the theoretical aspects of which are summarized in the following.

In order to select or learn features in a cognitive way, we want to have a method that can be applied completely autonomously, with no need for human supervision. One way of achieving this is to use dimensionality reduction (DR), where a data set X of size t×n is mapped onto a lower dimension data set Y of size t×p. In this context $\mathbb{R}^n$ is referred to as observation space and $\mathbb{R}^p$ as feature space. The idea is to identify or learn a higher dimensional manifold in a specific data set by creating a representation with a lower dimension.

Figure 15:
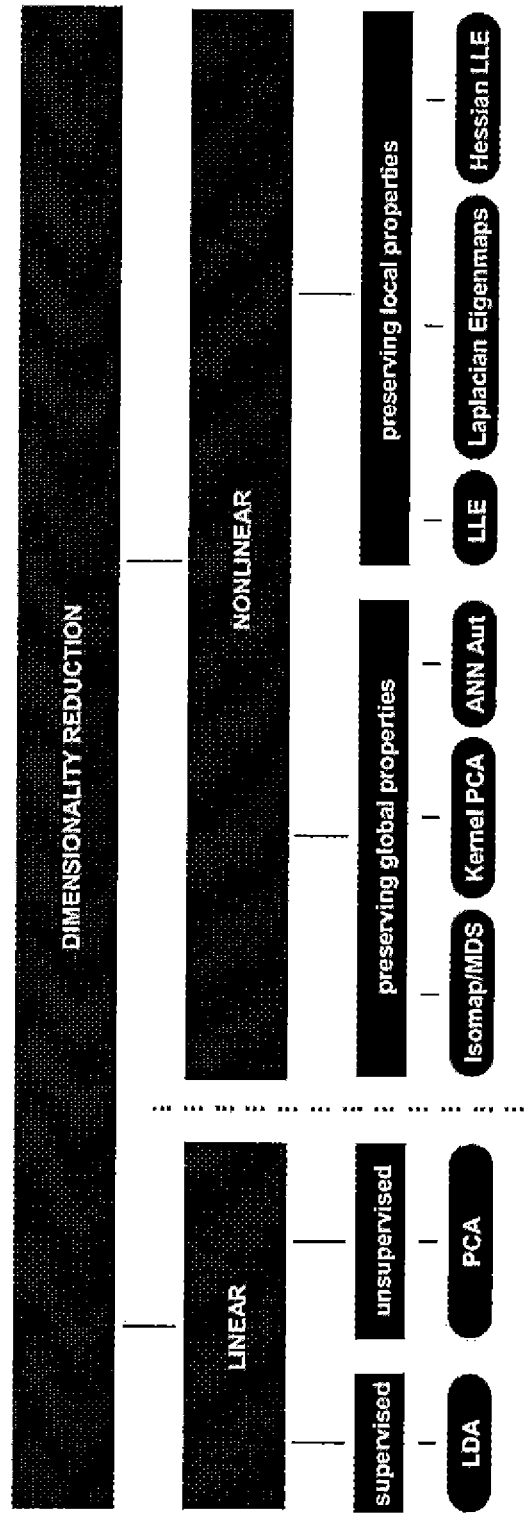
FIG. 15 shows categories of linear and nonlinear dimensionality reduction techniques.

Methods used to find features in a data set may be subdivided into two groups, linear and nonlinear, as shown in FIG. 15. Linear dimensionality reduction techniques seem to be outperformed by nonlinear dimensionality reduction when the data set has a nonlinear structure. This comes with the cost that nonlinear techniques generally have longer execution times than linear techniques do. Furthermore, in contrast to nonlinear methods linear techniques allow a straightforward approach of mapping back and forth. The question is whether a linear dimensionality reduction technique is sufficient for food processing, or if nonlinear techniques bring more advantages than costs. The following nonlinear techniques are very advantageous for artificial data sets: Hessian LLE, Laplacian Eigenmaps, Locally Linear Embedding (LLE), Multilayer Autoencoders (ANN Aut), Kernel PCA, Multidimensional Scaling (MDS), Isometric Feature Mapping (Isomap), and others. As a result Isomap proves to be one the best tested algorithms for artificial data sets. We find that the Isomap algorithm seems to be the most applicable nonlinear dimensionality reduction technique for food processing. Therefore Isomap and two linear dimensionality reduction techniques are introduced below.

Principal Component Analysis

Principal Component Analysis (PCA) enables the discovery of features that separate a data set by variance. It identifies an independent set of features that represents as much variance as possible from a data set, but are lower in dimension. PCA is known in other disciplines as the Karhunen-Loève transform and the part referred as Singular Value Decomposition (SVD) is also a well-known name. It is frequently used in statistical pattern or face recognition. In a nutshell, it computes the dominant eigenvectors and eigenvalues of the covariance of a data set. We want to find a lower-dimensional representation Y with t×p elements of a high-dimensional data set t×n mean adjusted matrix X, maintaining as much variance as possible and with decorrelated columns in order to compute a low-dimensional data representation $y_i$ for the data set $x_i$. Therefore PCA seeks a linear mapping $M_{PCA}$ of size n×p that maximizes the term $tr(M_{PCA}{}^T cov(X) M_{PCA})$, with $M_{PCA}{}^T M_{PCA} = I_p$ and cov(X) as the covariance matrix of X. By solving the eigenproblem with $$cov(X) M_{PCA} = M_{PCA} A, \quad \text{(Formula 2.3)}$$

we obtain the p ordered principal eigenvalues with the diagonal matrix given by $A = diag(\lambda_1, \ldots, \lambda_p)$. The desired projection is given by $$Y = X M_{PCA}, \quad \text{(Formula 2.4)}$$

gives us the desired projection onto the linear basis $M_{PCA}$. It can be shown that the eigenvectors or principal components (PCs) that represent the variance within the high-dimensional data representation are given by the p first columns of the matrix $M_{PCA}$ sorted by variance. The value of p is determined by analysis of the residual variance reflecting the loss of information due to dimensionality reduction.

By finding an orthogonal linear combination of the variables with the largest variance, PCA reduces the dimension of the data. PCA is a very powerful tool for analyzing data sets. However, it may not always find the best lower-dimensional representation, especially if the original data set has a nonlinear structure.

Linear Discriminant Analysis

Despite the usefulness of the PCA, the Linear Discriminant Analysis (LDA) may be seen as a supervised dimensionality reduction technique. It can be categorized as using a linear method, because it also gives a linear mapping $M_{LDA}$ for a data set X to a lower-dimension matrix Y, as stated for $M_{PCA}$ in equation 2.4. The necessary supervision is a disadvantage if the underlying desire is to create a completely autonomous system. However, LDA supports an understanding of the nature of the sensor data because it can create features that represent a desired test data set.

Because the details of LDA and Fisher's discriminant are known, the following is a brief simplified overview. Assume we have the zero mean data X. A supervision process provides the class information to divide X into C classes with zero mean data $X_c$ for class c. We can compute this with $$S_w = \sum_{c=1}^{C} cov(X_c), \quad \text{(Formula 2.5)}$$

the within-class scatter $S_w$, a measure for the variance of class c data to its own mean. The between-class scatter $S_b$ follows $$S_b = cov(X) - S_w. \quad \text{(Formula 2.6)}$$

Between-class scatter is a measure of the variance of each class relative to the means of the other classes. We obtain the linear mapping $M_{LDA}$ by optimizing the ratio of the between-class and within-class scatter in the low-dimensional representation using the Fisher criterion, $$J(M) = \frac{M^T S_b M}{M^T S_w M}. \quad \text{(Formula 2.7)}$$

Maximizing the Fisher criterion by solving the eigenproblem for $S_w^{-1} S_b$ provides C−1 eigenvalues that are non-zero. Therefore, this procedure seeks the optimal features to separate the given classes in a subspace with linear projections. LDA thus separates a low-dimensional representation with a maximized ratio of the variance between the classes to the variance within the classes.

Isometric Feature Mapping

The PCA and LDA methods produce linear mapping from a high-dimensional data set to a low-dimensional representation. This may be expressed as learning a manifold in an observation space and finding a representation for this in a lower-dimensional feature space. For data sets with a nonlinear structure, such as the artificial Swiss-roll data set, linear projections will lose the nonlinear character of the original manifold. Linear projections are not able to reduce the dimension in a concise way: data points in the feature space may appear nearby although they were not in the observation space. In order to address this problem, nonlinear dimensionality reduction techniques have recently been proposed relative to the linear techniques. However, it is a priori unclear whether nonlinear techniques will in fact outperform established linear techniques such as PCA and LDA for data from food processing sensor systems.

Isometric Feature Mapping or the Isomap algorithm attempts to preserve the pair-wise geodesic or curvilinear distances between the data points in the observation space. In contrast to a Euclidean distance, which is the ordinary or direct distance between two points that can be measured with a ruler or the Pythagorean theorem, the geodesic distance is the distance between two points measured over the manifold in an observation space. In other words, we do not take the shortest path, but have to use neighboring data points as hubs to hop in between the data points. The geodesic distance of the data points $x_i$ in observation space may be estimated by constructing a neighborhood graph N that connects the data point with its K nearest neighbors in the data set X. A pairwise geodesic distance matrix may be constructed with the Dijkstra's shortest path algorithm. In order to reduce the dimensions and obtain a data set Y, multidimensional scaling (MDS) may be applied to the pairwise geodesic distance matrix. MDS seeks to retain the pairwise distances between the data points as much as possible. The first step is applying a stress function, such as the raw stress function given by $$\Phi(Y) = \sum_{ij} (\|x_i - x_j\| - \|y_i - y_j\|)^2, \qquad \text{(Formula 2.8)}$$

in order to gain a measure for the quality or the error between the pairwise distances in the feature and observation spaces. Here, $\|x_i - x_j\|$ is the Euclidean distance of the data points $x_i$ and $x_j$ in the observation space with $y_i$ and $y_j$ being the same for the feature space. The stress function can be minimized by solving the eigenproblem of the pairwise distance matrix.

The Isomap algorithm thus reduces the dimension by retaining the pairwise geodesic distance between the data points as much as possible.

Classification for Machine Learning

In machine learning, it is not only the extraction of features that is of great scientific interest, but also the necessity of taking decisions and judging situations. Classification techniques may help a machine to differentiate between complicated situations, such as those found in food processing. Therefore classifiers use so-called classes that segment the existing data. These classes can be learned from a certain training data set. In the ongoing research into AI and cognitive machines, Artificial Neural Networks were developed relatively early in the process. In comparison, the concepts of Kernel Machines and reinforcement learning appeared only recently but showed increased cognitive capabilities.

Artificial Neural Networks

Artificial Neural Networks (ANN) have been discussed extensively for decades. ANN was one of the first successes in the history of Artificial Intelligence. Using natural brains as models, several artificial neurons are connected in a network topology in such a way that an ANN can learn to approximate functions such as pattern recognition. The model allows a neuron to activate its output if a certain threshold is reached or exceeded. This may be modeled using a threshold function. Natural neurons seem to "fire" with a binary threshold. However, it is also possible to use a sigmoid function, $$f(x) = \frac{1}{1 + e^{-vx}}, \qquad \text{(Formula 2.9)}$$

with v as parameter of the transition. For every input connection, an adjustable weight factor $w_i$ is defined, which enables the ANN to realize the so-called learning paradigm. A threshold function o can be expressed using the weight factors W and the outputs from the preceding neurons P, $o = W^T P$, with a matrix-vector notation. The neurons can be layered in a feedforward structure, Multi-Layer Perceptron (MLP) or, for example, with infinite input response achieved using feedback loops with a delay element in so-called Recurrent Neural Networks. A MLP is a feedforward network with a layered structure; several hidden layers can be added if necessary to solve nonlinear problems. The MLP can be used with continuous threshold functions such as the sigmoid function in order to support the backpropagation algorithm stated below for supervised learning. This attempts to minimize the error E in $$E = \frac{1}{2} \sum_i (z_i - a_i)^2, \qquad \text{(Formula 2.10)}$$

from the current output $a_i$ of the designated output $z_i$, where the particular weights are adjusted recursively. For an MLP with one hidden layer, if $h_j$ are hidden layer values, $e_i$ are input values, $\alpha \geq 0$ is the learn rate, and $\epsilon_i = z_i - a_i$, then the weights of the hidden layer $W_{ij}^1$ and the input layer $W_{ij}^2$ are adjusted according to, $$\Delta w_{ij}^1 = \alpha \epsilon_i h_j, \qquad \text{(Formula 2.11)}$$

$$\Delta w_{ij}^2 = \alpha \sum_m e_m w_{mi}^1 e_j. \qquad \text{(Formula 2.12)}$$

The layers are enumerated starting from the input to the output. For backpropagation, the weights are adjusted for the corresponding output vectors until the overall error cannot be further reduced. Finally, for a classification of C classes, the output layer can consist of either C output neurons, representing the probability of the respective class, or a single output neuron that has defined ranges for each class.

ANN can thus learn from or adapt to a training data set and can find a linear or a nonlinear function from N input neurons to C output neurons. This may be used for classification to differentiate a set of classes in a data set.

Kernel Machines

In general, a classification technique should serve the purpose of determining the probability of learned classes occurring based on the measured data. Classification can be mathematically formulated as a set of classes $c_i = c_1, \ldots, c_N$ in C, with a data set represented by $x_i \in \mathbb{R}^n$, and a probability of $p_i$, $$p_i = p(c_i | x_i) = f_c(x_i, \theta). \qquad \text{(Formula 2.13)}$$

The parameter $\theta$ may then be chosen separately for every classification or can be learned from a training data set.

In order to achieve learning, it is desirable to facilitate efficient training algorithms and represent complicated nonlinear functions. Kernel machines or Support Vector Machines (SVM) can help with both goals. A simple explanation of SVM, or in this particular context Support Vector Classification (SVC), is as follows: in order to differentiate between two classes, good and bad, we need to draw a line and point out which is which; since an item cannot be both, a binary decision is necessary, $c_i \in \{-1, 1\}$. If we can only find a nonlinear separator for the two classes in low-dimensional space, we can find a linear representation for it in a higher-dimensional space, a hyperplane. In other words, if a linear separator is not possible in the actual space, an increase of dimension allows linear separation. For instance, we can map with function F a two-dimensional space $f_1=x_1$, $f_2=x_2$ with a circular separator to a three-dimensional space $f_I=x_1^2$, $f_{II}=x_2^2$, $f_{III}=\sqrt{2}x_1x_2$ using a linear separator, as illustrated in FIG. 16.

SVC seeks for this case an optimal linear separator, a hyperplane, $$H=\{x\in\mathbb{R}^3 | ox+b=0\} \quad \text{(Formula 2.14)}$$

in the corresponding high-dimensional space for a set of classes $c_i$. In three-dimensional space, these can be separated with a hyperplane, H, where o is a normal vector of H, a perpendicular distance to the origin $|b|/\|o\|$, and o with an Euclidean norm of $\|o\|$. In order to find the hyperplane that serves as an optimal linear separator, SVC maximizes the margin given by, $$d(o, x_i; b) = \frac{|ox_i + b|}{\|o\|}, \quad \text{(Formula 2.15)}$$

between the hyperplane and the closest data points $x_i$. This may be achieved by minimizing the ratio $\|o\|^2/2$ and solving with the optimal Lagrange multiplier parameter $\alpha_i$. In order to do this, the expression, $$\sum_{i=1}^{l} \alpha_i + \frac{1}{2}\sum_{j=1}^{l}\sum_{k=1}^{l} \alpha_i\alpha_j c_i c_j (x_i \cdot x_j), \quad \text{(Formula 2.16)}$$

has to be maximized under the constraints $\alpha_i \geq 0$ and $\Sigma_i \alpha_i c_i = 0$. The optimal linear separator for an unbiased hyperplane is then given using, $$f(x) = \text{sign}\left(\sum_i \alpha_i c_i (x \cdot x_i)\right), \quad \text{(Formula 2.17)}$$

allowing a two-class classification.

SVM has two important properties: it is efficient in computational runtime and can be demonstrated with equations 2.16 and 2.17. First, the so-called support vectors or set of parameters $\alpha_i$ associated with each data point is zero, except for the points closest to the separator. The effective number of parameters defining the hyperplane is usually much less than 1, increasing computational performance. Second, the data enter expression 2.16 only in the form of dot products of pairs of points. This allows the opportunity of applying the so-called kernel trick with $$x_i \cdot x_j \mapsto F(x_i) \cdot F(x_j) = K(x_i, x_j) \quad \text{(Formula 2.18)}$$

which often allows us to compute $F(x_i) \cdot F(x_j)$ without the need of knowing explicitly F. The kernel function $K(x_i, x_j)$ allows calculation of the dot product to the pairs of input data in the corresponding feature space directly. However, the kernel function applied throughout the present invention is the Gaussian Radial Basis Function and has to fulfill certain conditions, as in $$K_G(x_i, x_j) = e^{-\gamma\|x_i - x_j\|^2}, \quad \text{(Formula 2.19)}$$

with γ as the adjustable kernel parameter.

Because we have so far discussed only binary decisions between two classes, we note here that it is also possible to enable soft and multi-class decisions. The latter can be achieved in steps by a pairwise coupling of each class $c_i$ against the remaining n−1 classes.

SVC can thus be used to learn complicated data. It structures this data in a set of classes in a timely fashion. Mapping into a higher-dimensional space and finding the optimal linear separator enables SVM to use efficient computational techniques such as support vectors and the kernel trick.

Fuzzy K-Nearest Neighbor

Unlike the previously discussed Support Vector Machines, a less complicated but highly efficient algorithm called the Fuzzy K-Nearest Neighbor (KNN) classifier can also separate classes within data. The algorithm can categorize unknown data by calculating the distance to a set of nearest neighbors.

Assume we have a set of n labeled samples with membership in a known group of classes. If a new sample x arrives, it is possible to calculate membership probability $p_i(x)$ for a certain class with the vector's distance to the members of the existing classes. If the probability of membership in class A is 90% compared to class B with 6% and C with just 4%, the best results seem to be apparent. In contrast, if the probability for membership in class A is 45% and 43% for class B, it is no longer obvious. Therefore KNN provides the membership information as a function to the K nearest neighbors and their membership in the possible classes. This may be summarized with $$p_i(x) = \frac{\sum_{j}^{K} P_{ij}\left(\frac{1}{\|x-x_j\|^{\frac{2}{m-1}}}\right)}{\sum_{j}^{K} \frac{1}{\|x-x_j\|^{\frac{2}{m-1}}}}, \quad \text{(Formula 2.20)}$$

where $p_{ij}$ is the membership probability in the ith class of the jth vector within the labeled sample set. The variable m is a weight for the distance and its influence in contributing to the calculated membership value.

When applied, we often set m=2 and the number of nearest neighbors K=20.

Reinforcement Learning

In contrast to previous learning methods, which learn functions or probability models from training data, reinforcement learning (RL) can facilitate learning using environmental feedback from an agent's own actions in the long-term, without the need for a teacher. This entails the difference between supervised and unsupervised learning. If a long-term goal is sought, positive environmental feedback, also known as reward or reinforcement, may support improvement. An agent may learn from rewards how to optimize its policy or strategy of interacting with the real world, the best policy being one that optimizes the expected total reward. RL does not require a complete prior model of the environment nor a full reward function. The artificial agents therefore indicate cognitive capability and act in a similar manner to animals, which may learn from negative results like pain and hunger and from positive rewards like pleasure and food. In this case we pick that the agent has to use a value function approach, in which it attempts to maximize its environmental return.

In RL, an agent takes actions, $a_t$, in an environment that it perceives to be its current state, $s_t$, in order to maximize long-term rewards, $r_t$, by learning a certain policy, $\pi$. However, before we can start learning with reinforcement we have to find answers regarding the appropriate agent design. The agent could try to maximize the expected return by estimating the return for a policy $\pi$. This agent behavior is also referred to as value function estimation. The agent may evaluate the action by estimating the state value using a state-value function $V_\pi(s)$, considering a certain policy $\pi_w$ that is continuously differentiable, as in $$V_\pi(s) = E\left(\sum_{i=0}^{\infty} \gamma^i r_i \,\middle|\, s_0 = s\right). \quad \text{(Formula 2.21)}$$

Using this function the agent may estimate the expected return for a given state and a following policy. It could also estimate the expected return for an action, following a given state and policy. Therefore, the agent chooses an action considering the given state from the state-action function or Q-function, as in $$Q_\pi(s, a) = E\left(\sum_{t=0}^{\infty} \gamma^t r_t \,\middle|\, s_0 = s, a_0 = a\right). \quad \text{(Formula 2.22)}$$

The next action therefore relies on a reward function $r_t$ and in order to allow the agent to grant a concession for expected future rewards over current rewards, the discount factor $0 \le \gamma \le 1$ may be selected. It is possible to set how much the agent should discount for future rewards, for instance future rewards are irrelevant for $\gamma=0$.

In RL, the methods may be subdivided into groups such as value function based methods or direct policy search. Many different actor-critic algorithms are value function based methods, estimating and optimizing the expected return for a policy. In order to realize a value function based method, the behavior for an artificial agent and the underlying control problem may be stated as a Markov decision process (MDP). The system perceives its environment over the continuous state set, where $s_t \in \mathbb{R}^k$ and $s_o$ as the initial state. It can choose from a possible set of actions $a_t \in \mathbb{R}^m$ in respect to a stochastic and parameterized policy defined as $\pi(a_t|s_t) = p(a_t|s_t, w_t)$, with the policy parameters $w \in \mathbb{R}^k$. With a learned policy, it can be mapped from states to actions with respect to the expected rewards $r_t \in \mathbb{R}$. The reward after each action relies on $r_t(s_t, a_t)$. If no environmental model is available, the mentioned actor-critic methods can potentially develop policy-finding algorithms. The name is derived from the theater, where an actor adapts its actions in response to feedback from a critic. This can be obtained using a given evaluation function as a weighted function of a set of features or a so-called basis function $\phi(s)$, which then gives the approximation of the state-value function with value function parameters v, as in $$V_\pi(s) = \theta(s)^T v. \quad \text{(Formula 2.23)}$$

Improving the policy is an optimization issue that may be addressed with a policy gradient. The choice of the policy gradient method is critical for convergence and efficiency. Both seem to be met by the Natural Actor-Critic (NAC) algorithm, as described by J. Peters and S. Schaal, "Natural actor-critic", Neurocomputing, Vol. 71, no 7-9, pp. 1180-1190, 2008, where the actor improves using the critic's policy derivative g as in equation 2.24, $$g = \nabla_w \log \pi(a_i|s_i). \quad \text{(Formula 2.24)}$$

The steps for improvement of policy parameters of the NAC algorithm are then calculated using, $$w_{t+1} = w_t + \alpha \hat{g}, \quad \text{(Formula 2.25)}$$

where $\alpha$ is the learning rate, and $\hat{g}$ is the natural gradient calculated using the Fisher metric or is derived from the policy as demonstrated within the mentioned NAC algorithm publication. The NAC algorithm with LSTD-Q is fully documented at table 1 on page 1183 of J. Peters and S. Schaal, "Natural actor-critic", Neurocomputing, vol. 71, no. 7-9, pp. 1180-1190, 2008. It is applied with a parameterized policy $\pi(a|s) = p(a|s, w)$ initial parameters $w = w_0$ comprising the following steps in pseudo code:

1: START: Draw initial state $s_0 \sim p(s_t)$ and select parameters $A_{t+1} = 0$; $b_{t+1} = z_{t+1} = 0$
2: For $t = 0, 1, 2, \ldots d_o$
3: Execute: Draw action $a_t \sim \pi(a_t|s_t)$, observe next state $s_{t+1} \sim p(s_{t+1}|s_t, a_t)$, and reward $r_t = r(s_t, a_t)$.
4: Critic Evaluation (LSTD-Q($\lambda$)): Update
4.1: basis functions: $\hat{\phi}_t = [\phi(s_{t+1})^T, 0^T]^T$, $\tilde{\phi}_t = [\phi(s_t)^T, \nabla_w \log \pi(a_t|s_t)^T]^T$,
4.2: statistics: $z_{t+1} = \lambda z_t + \tilde{\phi}_t$; $A_{t+1} = A_t + z_{t+1}(\tilde{\phi}_t - \gamma \hat{\phi}_t)^T$; $b_{t+1} = b_t + z_{t+1} r_t$,
4.3: critic parameters: $[v_{t+1}^T, \hat{g}_{t+1}^T]^T = A_{t+1}^{-1} b_{t+1}$,
5: Actor: If gradient estimate is accurate, update policy parameters
5.1: wt+1=wt+$\alpha \hat{g}$ t+1 and forget (reset) statistics. END.

The basis functions $\phi(s)$ may be represented by mapping the sensor data input into a feature space as we discussed it elsewhere in this document. In this case the basis functions are equal to the feature values. The basis functions may as well be chosen differently or the agent may use raw sensor data. The basis function may as well incorporate adaptive methods or an own learning step, that maximizes with the reward function results.

It is important to note that other RL agents are applicable as well. Many other policy learning agent concepts may be applied. It furthermore is inventive to use other sources as reward signal $r_t$ besides the classification output or quality indicator. For instance it is possible to apply a post-process or pre-process sensor as reward signal source. The reward function could be the probability value between 0 and 1 or −1 to 1 of a measured data of a post-process sensor to be part of a good or bad class, which is determined by a classifier as described above. In case a pre-process sensor is used for giving a reward $r_t$. An RL agent could find a parameter set to achieve this goal. Thus reinforcement learning may be a step towards a long-term goal in that it entails learning a policy from given rewards using policy-finding algorithms such as the Natural Actor-Critic.

Cognitive Technical Architecture

An artificial agent is anything that perceives its environment through sensors and acts in consequence of this through actuators. An agent is defined as an architecture with a program. The inspirational role model for this is natural cognition, and we want to realize a similar acting cognition for technical systems. Therefore, the agent will be equipped with cognitive capabilities, such as abstracting information, learning, and decision making for a manufacturing workstation. As part of the process, this section introduces an architecture that creates and enables agents to manage production tasks. In order to do so, the agents follow a cognitive perception-action loop, by reading data from sensors and defining actions for actuators.

A natural cognitive capability is the capacity to abstract relevant information from a greater set of data and to differentiate between categories within this information. Transferring this concept from natural cognition to the world of mathematical data analysis, a combination of data reduction techniques and classification methods is used according to the present invention to achieve something that exhibits similar behavior. In industrial production, many manufacturing processes can be carried out using a black box model, focusing on the ins and outs of the box rather on than what actually happens inside. The connections to the black box that may be used in production systems are generally sensors and actuators. Sensors such as cameras, microphones, tactile sensors, and others monitor the production processes. These systems also need actuators, such as linear drives or robotic positioning, in order to interact with its environment. For every production process, these actuators have to be parameterized. In order to learn how an agent can adaptively control at least one parameter of these production systems, many combinations of self-learning algorithms, classification techniques, knowledge repositories, feature extraction methods, dimensionality reduction techniques, and manifold learning techniques could be used. The present invention provides also different controlling techniques, both open- and closed-loop, using multiple different sensors and actuators. After many simulations and experiments, a simple architecture that demonstrates how these techniques may be combined proved to be successful and reliable, at least for food processing. However, the food processes may be interpreted as a form of black box, and may thus be applicable to other types of production processes.

Figure 17:
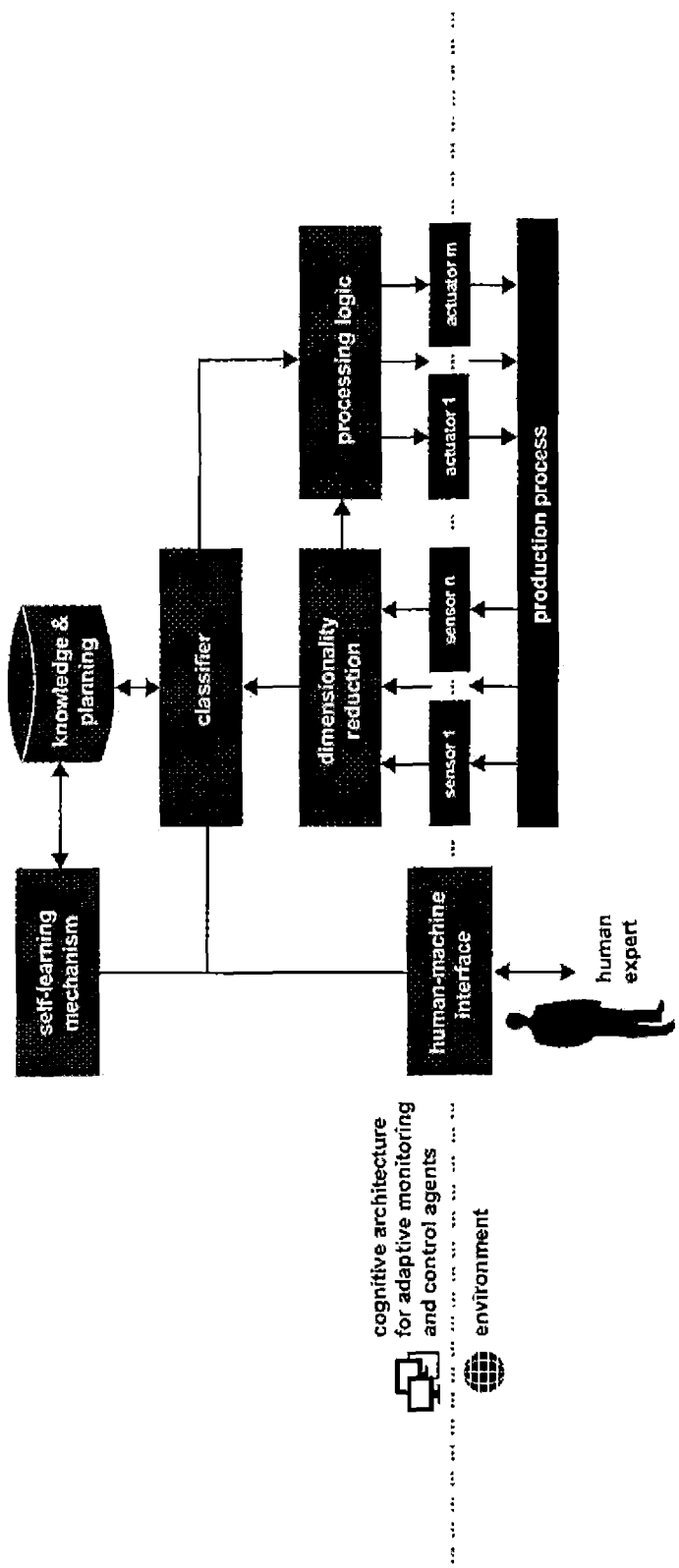
FIG. 17 shows an architecture according to the present invention and component groups to design agents for process monitoring or closed-loop control in food production systems using a black-box model with sensors and actuators.

FIG. 17 illustrates a cognitive architecture that may be suitable for designing agents that can provide monitoring or adaptive process control for production tasks. The diagram describes the unit communication and information processing steps. Natural cognition seems to abstract information firstly by identifying representative symbolism, such as structured signals. A similar process can be accomplished using dimensionality reduction (DR), in which the agent uses a low-dimensional representation of the incoming sensor data. Natural cognition then recognizes whether or not knowledge about the incoming sensational events is already present. This step may be achieved by using classification techniques that categorize "sensorial" events or characteristics. A natural subject may decide to learn or to plan new actions. In order to replicate this, the architecture of the present invention offers self-learning techniques that feeds a processing logic. In seeking to achieve quick reactions without the need to start a complex decision-making process, we may also "hard-wire" a sensor input that can directly initiate an actuator in using a closed-loop control design. Therefore, the architecture of the present invention may be designed in respect to four modes of usage, which will be discussed individually in the following: first, abstracting relevant information; second, receiving feedback from a human expert on how to monitor and control processes, or supervised learning; third, acting on learned knowledge; and fourth, autonomously controlling processes in previously unknown situations.

As with other cognitive architectures the aim here is creating agents with some kind of artificial intelligence or cognitive capabilities related to humans.

The agents may be composed of several components from different dimensionality reduction and classification techniques, which allow us to compare the performance of composed agents and modules in terms of overall food processing quality. Many different dimensionality reduction and classification techniques may be applicable, and some of these have been evaluated in the research project. The cognitive architecture of the present invention offers the following modules for composing agents: Principal Component Analysis (PCA), Linear Discriminant Analysis (LDA), Isometric Feature Mapping (Isomap), Support Vector Machines (SVM), Fuzzy K-Nearest Neighbors (KNN), Artificial Neural Networks (ANN), and reinforcement learning (RL), along with some other methods. Three embodiments of the present invention of control agents within this architecture would be agent A connecting Isomap, SVM, ANN, and PID energy supply control, or agent B connecting Isomap, SVM, and PID energy supply control, or agent C connecting ANN and Fuzzy KNN, for control.

Abstract Relevant Information

In natural human cognition, we abstract or absorb information from everything that we hear, feel, and see. Therefore, we only generally remember the most interesting things. Inspired by this, a technical cognitive system should similarly abstract relevant information from a production process. Working with abstracted features rather than with raw sensor data has certain advantages. Many weak sensor signals may be reduced in dimension to fewer but better signals, resulting in a more reliable feature. Additionally, in order to realize real-time process control, it is necessary to reduce the volume of the incoming sensor data because a greater amount of data may have a significant influence in causing longer execution times for the entire system.

The architecture of the present invention requires a test run in order to abstract initial information. During this period of agent training, the parameter range of the actuator that will be controlled is altered. In order to determine which information is most relevant, the agent should explore its own range of actions. After the initial reference test, the system analyzes the recorded sensor data in order to discover representative features. The agent may solve feature calculations separately for different kinds of sensors, but the sensory units should ideally be trained to map the sensory input into the learned feature space. Finding a useful representation of the feature space is critical because the system will only be able to recognize or react to changes in the feature values. The purpose of the cognitive processing of the present invention is to provide as much information as possible for the subsequent processing steps. However, the raw sensor data contains repetitions, correlations, and interdependencies that may be neglected. Therefore, in order to abstract the relevant information, the most significant features, or those that contain the most information, should be identified. In order to do this "cognitively", an agent should perform this task without the necessary supervision of a human expert. Therefore, a method of feature extraction is chosen that can be applied to all of the different kinds of processing tasks and the corresponding sensor data without the need to change parameterization or re-configuration. Manifold learning or dimensionality reduction techniques satisfy this need. They can reduce a sensor data set X of dimension n in observation space to a data set Y of dimension P in feature space. Often, the new quantity P is much less than n. However, many linear and nonlinear dimensionality reduction techniques have been tried and tested for different purposes. The present invention provides a suitable feature extraction technique for production workstations, complying with the following requirements the feature extraction method works transparently and is able to display the processing steps to the user. The feature extraction method is able to run unsupervised. The feature extraction method is executable within a reasonable time-frame for configuration, especially during processing. The extracted features contain enough process information for reliable classification within several food loads.

In essence, PCA seeks orthogonal linear combinations that represent a greater data set. These may be calculated for incoming sensor data vectors. These eigenvectors may serve as features for classification up to a threshold d. Feature extraction combined with classification may be achieved using Linear Discriminant Analysis. Analyzing the same data set using LDA and three learned quality classes defined as "good", "medium", and "bad" provides another set of features. Feature extraction may also be achieved using the Isomap algorithm. Unfortunately, the nonlinear feature cannot be displayed in the same way as the linear feature extraction of LDA and PCA. The extracted features of the methods named above are compared in the following. The LDA feature seems to contain more details than any one of the PCA features. Using this method of calculating, the LDA features seem to contain more process information in fewer features than PCA because they are especially designed to separate the desired classes. Furthermore, it is possible to display the calculated features using PCA and LDA in a way that makes these two methods more transparent than Isomap. The user gets an idea of what a process looked like if a feature is identified in a process video simply by looking at it. PCA and Isomap have the advantage that they can run unsupervised, which is not possible with LDA. Therefore, LDA merely serves as a comparison to PCA, but is not considered as an alternative for the desired architecture. Furthermore, the LDA feature seems to be very individualized for a particular process. Isomap has considerably higher execution times for analysis and out-of-sample extension. Therefore, if classification with PCA achieves sufficient results, then it is more applicable to the system under research. Therefore, the method of choice would be PCA, unless Isomap shows a significantly better performance toward the first object of the present invention. We have to postpone the final choice of dimensionality reduction techniques because the most important quality measures are the experimental results, which are the basis of the present invention.

In essence, dimensionality reduction may allow agents to abstract relevant information in terms of detecting variances and similarities during a training trial. This helps the agent to process only a few feature values compared to the significantly higher volume of raw sensor data. Furthermore, dimensionality reduction may support the perception of similarities in unknown situations, for instance similar food processing characteristics such as food size and form, even if these have not been part of the training. This may improve the adaptability of the agents to unknown but similar situations.

Supervised Learning from Human Experts

In natural human cognition, for instance in childhood, we often learn from others how to manage complex tasks. Similarly, a machine should have the possibility of learning its task initially from a human expert. Supervised learning seems to be the most efficient way of setting up a cognitive agent for production. In industrial production, a qualified human supervisor is usually present when the production system is being installed or configured. The architecture that we are examining uses human-machine communication in order to receive feedback from an expert, for instance through an intuitive graphical user interface on a touchscreen tablet computer. As mentioned above, at least one test action per actuator or test run is needed in this architecture as an initial learning phase. During these tests, the agent executes one actuator from within the desired range of actions, and the sensor data input is stored. After this run, an expert provides feedback concerning whether the robot has executed the actuator correctly, or if the action was unsuccessful or undesirable. The feedback may come in many different categories so that different kinds of failures and exit strategies may be defined. A classification technique may then collect the features together with the corresponding supervisory feedback. Combined with lookup tables, the classifier module will serve as knowledge and as a planning repository for a classification of the current system state. How an agent may perform its own actions and give itself feedback will be of importance for the next section; this section mainly covers the cognitive capability of learning from a human expert, and the application of this knowledge for monitoring purposes.

Support Vector Machines, Fuzzy K-Nearest Neighbor, and Artificial Neural Networks as classification techniques have been discussed. The more that the human expert teaches the machine, the likelier it is that the system will achieve the desired goal. In order to save costs, the necessary human supervisor time should be minimized to just one or two reference tests, if possible.

Semi-Supervised Learning

The previous discussion shows how agents in the investigated cognitive architecture perceive their surroundings and learn from a human expert, as well as displaying their knowledge in terms of monitoring. The provided monitoring signal based on selected features is obtained from different sensors that are interpreted using a trained classifier. This monitoring signal seems to have improved quality and may be applicable to the control of process parameters. The agent would then change its position from observing the processing to actually acting upon the gained knowledge. However, if an agent is also applicable to process control in industrial processing, it has to fulfill many requirements with a performance close to perfection. The following are some of the requirements for the underlying cognitive architecture: The process control module should be capable of completing at least one control-cycle from sensor input to actuator output. The controlled parameter should have an effect on the process outcome when altered, while simultaneously responding in a timely fashion. The process control module should be optimized in terms of providing a balance of reliable stability and necessary dynamics.

In order to realize a robust process control that is suitable for industrial production processes, a fast or real-time closed-loop control is often required. The advantage of the architecture under investigation is that the use of features rather than raw sensor data permits faster completion of control-loops with a minimal loss of information. In this architecture, any kind of controller design may be implemented that fits with the classification output. A simple version would have three possible classification output values: under baked, class I; correct, class II; and over baked, class III. This may be expressed using $$y_e = [-1\ 0\ 1] \begin{bmatrix} p_I \\ p_{II} \\ p_{III} \end{bmatrix}, \quad \text{(Formula 3.1)}$$

where p are the class probabilities and $y_e$ the quality indicator.

A PID controller could adjust a parameter of the system's actuators according to the monitoring signal discussed above concerning supervised learning from human experts. Combining PID-control with the classification results enables the agents to perform energy supplied controlled processing. This can be realized as shown in $$c_t = pe_t + I \sum_{i=t-n}^{t-1} e_i + D(e_t - e_{t-1}),$$ (Formula 3.2)

with P for proportional, I for integral, and D for derivative behavior. The goal is to minimize the error $R_c$ between the quality indicator $y_e$, the output of the classification module, and the desired value of 0.0. In this context, the inventive applicability of the desired value in dependency of a probability class related quality indicator gives the opportunity to vary this value to optimize the desired process results. One approach describes a PID control with an ANN and corresponding experiments. Another investigates the usage of an SVM classification module to control food processing.

Unsupervised Learning

As suggested, a self-learning mechanism is integrated into the system of the present invention. A novelty check on the basis of the trained features can detect new or previously unknown situations. In these cases, the system performs another test action and classifies the new food using the previously trained features. This time, it does not need to consult a human expert; it can map the gained knowledge onto the new food autonomously and can adjust the process control appropriately.

In order to achieve process feedback control, the monitoring signal $y_s$ is used as the control variable. As actuating variable, which could possibly be any alterable process parameter with interrelationship to $y_s$, the energy supply seems suitable for its low inertia and its strong relation to $y_A$. Its magnitude is calculated by the PID algorithm as shown in equation 3.2. In order to achieve process control, the agent closes the loop by connecting the monitoring signal to a PID controller, as is shown in equation 3.2. The feedback controller is designed as a single-input-single-output (SISO) control system, which receives the monitoring signal $y_s$ from the classification unit, with $0 < y_s \le 1$ for too low and $-1 \le y_s < 0$ for too high energy supply, and uses this as reference value to minimize controller error.

The previous description outlined how the cognitive agents learned from human expert feedback. It should be possible for the cognitive system to learn from its own actions, or to give itself feedback. This kind of cognitive capability may be attained with reinforcement learning (RL). A classifier may take over the role of giving feedback and provide a RL agent with rewards for its own actions. The agent then learns a policy on how to act or how to bake based on the feedback or on rewards received for its previous performance. In order to test this, the learning task is therefore for the agent to learn how to process food on the basis of gained knowledge at different velocities without further human expert supervision.

In order to achieve the given learning task using reinforcement learning, a reliable reward function is needed. As the system has multiple sensor data inputs, a classifier identifying features of a good baking, such as a Support Vector Machine, may serve as reward function $r_t$, as is shown in FIG. 23. These rewards may fulfill the role of a critic in the Natural Actor-Critic method, which is described before. Therefore, the next action that the agent chooses is absolute energy supply, $a_t$. The chosen action depends on the learned policy, as is shown in $$\pi(a_t|s_t) = p(a_t|s_t, w_t).$$ (Formula 4.1)

The policy parameters $w_t$ relies on the gradient $\hat{g}$ and $w_{t-1}$, as in equation 2.25. However, for a full review of the applied algorithm please consult the Natural Actor-Critic Algorithm with least-squares temporal difference learning, LSTD-Q ($\lambda$). The policy should enable the agent to map from states, $s_t$, to actions, $a_t$, by learning from rewards, $r_t$. The rewards naturally influence the policy parameters. The best policy of the RL agent of the present invention under investigation has been found with a sigma function, $$\pi(\phi(a_t|s_t)) = L_m \frac{1}{1 + e^{-w_t^T \phi(s_t)}} + \eta \Rightarrow a_{t+1},$$ (Formula 4.2)

where $L_m$ is the maximum allowed power and $\eta$ is the exploration noise determined by the product of a random number from −1 to 1 and the exploration parameter $\epsilon$. The present invention has investigated modules that are suitable for a cognitive architecture for food production machines within a cognitive perception-action loop connecting sensors and actuators. Cognitive capabilities are: to abstract relevant information; to learn from a human expert; to use the gained knowledge to make decisions; and to learn how to handle situations that the agent has not previously been trained in.

As already mentioned above the previously discussed machine learning techniques may be implemented in any herein described embodiment of a heat treatment monitoring system.

Figure 18A:
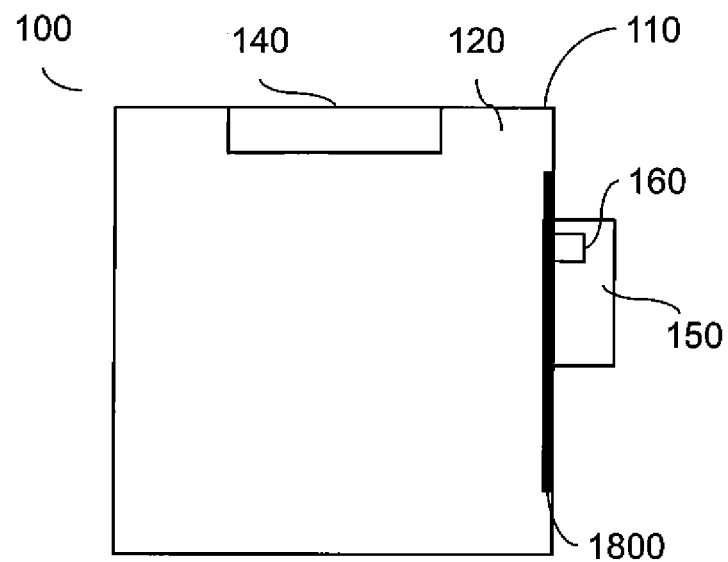
FIG. 18A shows a schematic cross sectional view of an embodiment of a heat treatment monitoring system.

In the following, an embodiment of a heat treatment monitoring system 100 illustrated in FIGS. 18A and 18B will be described. The heat treatment monitoring system comprises an oven 100 and a monitoring apparatus 150 as described above with regard to FIGS. 1A and 1B. The embodiment as described with regard to FIG. 18A should, however, not be restricted to the usage of the window 130 as described above, thus any kind of window 1800 adapted to permit the camera 160 to observe the food to be heated may be used. The embodiment of the monitoring apparatus 150 should further not be restricted to the employment within the embodiment of FIGS. 1A and 1B, but may be further employed within baking or pre-baking lines or food heating lines as described with regard to FIG. 8 to 10 or in any other embodiment as described above.

Figure 18B:
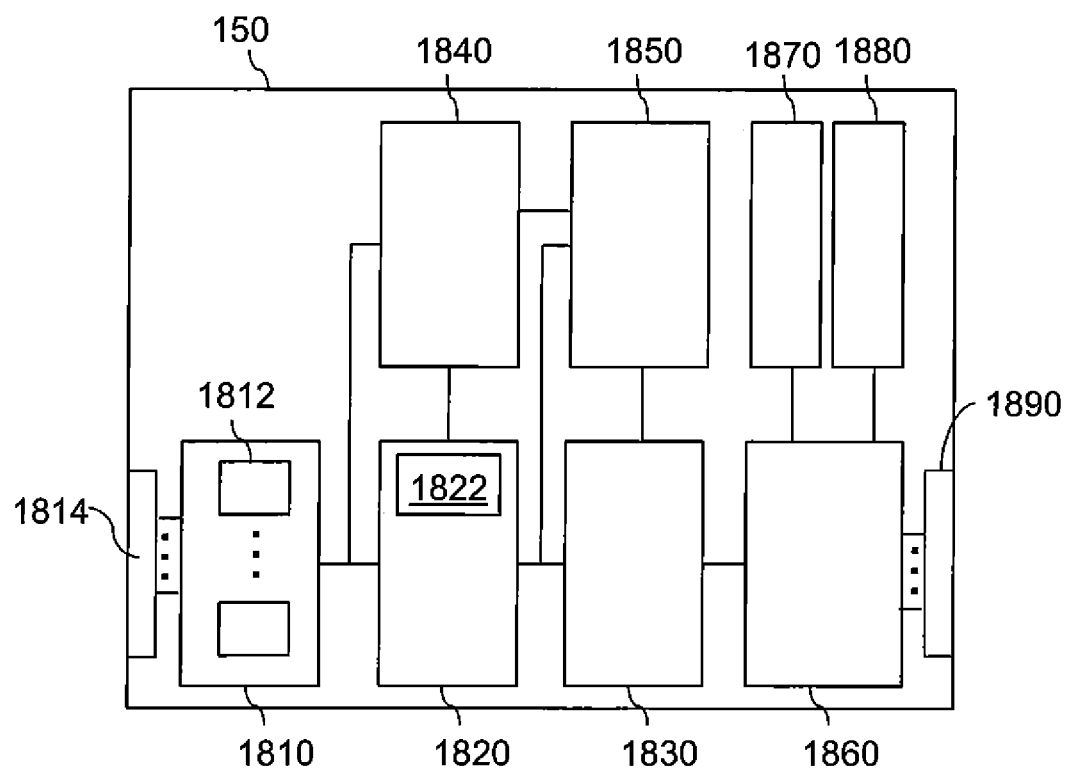
FIG. 18B shows a block diagram of an embodiment of a heat treatment monitoring system.

A block diagram of an embodiment of the monitoring apparatus 150 is shown in FIG. 18B. The monitoring apparatus 150 and the monitoring system 100, accordingly, comprises a sensor unit 1810 having at least one sensor 1815 to determine current sensor data of food being heated, a processing unit 1820 to determine current feature data from the current sensor data, and a monitoring unit 1830 adapted to determine a current heating process state in a current heating process of monitored food by comparing the current feature data with reference feature data of a reference heating process. The heat treatment monitoring system further comprises a learning unit 1840 adapted to determine a mapping of current sensor data to current feature data, and to determine reference feature data of a reference heating process based on feature data of at least one training heating process. The monitoring apparatus 150 further comprises a classification unit 1850 adapted to classify the type of food to be heated and to choose a reference heating process corresponding to the determined type of food. It should be emphasized that the respective units 1820, 1830, 1840, and 1850 may be provided separately or may also be implemented as software being executed by a CPU of the monitoring apparatus 150.

The sensor unit 1810 comprises at least one sensor 1812, wherein a sensor 1812 may be any sensor as described in the description above, in particular a camera 160 as described with respect to FIGS. 1A and 1B, any sensor of the sensor system 850 described with respect to FIG. 7 or 8 or the sensor system described with regard to FIG. 12. In particular, the at least one sensor 1812 of the sensor unit 1810 comprises at least one of hygrometer, insertion temperature sensor, treatment chamber temperature sensor, acoustic sensors, scales, timer, camera, image sensor, array of photodiodes, a gas analyser of the gas inside the treatment chamber, means for determining temperature profiles of insertion temperature sensors, means for determining electromagnetic or acoustic process emissions of the food to be treated like light or sound being reflected or emitted in response to light or sound emitters or sources, means for determining results from 3D measurements of the food to be heated including 3D or stereo camera systems or radar, or means for determining the type or constitution or pattern or optical characteristics or volume or the mass of the food to be treated. According to this embodiment it is beneficial to use as much sensor data as input as feasible. Which sensor signal provides the best information is hard to predict. As the algorithms detect the variance of a reference bake, the learning unit 1840 used to implement machine learning may choose different sensor data for individually different baking products. Sometimes, volume and color variance may be the most significant data, sometimes it may be humidity, temperature and weight.

In an embodiment, the sensor unit 1810 comprises the camera 160 as the only sensor 1812, which leads to the advantage that no further sensor has to be integrated in the monitoring apparatus 150. Thus, the monitoring apparatus 150 may be formed as a single and compact casing being mounted to an oven door of the oven 110. It is, however, also possible to provide a sensor data input interface 1814 at the monitoring apparatus 150, by which current sensor data of the above mentioned sensors can be read by the sensor unit 1810 and transferred to the processing unit 1820. The current sensor data of the sensors 1812 are not necessarily raw data but can be pre-processed, like HDR pre-processed pixel data of the camera 160 or pre-processed sensor data of the laser triangulation sensors, which may contain, e.g. a calculated value of volume of the observed food piece.

The processing unit 1820, the monitoring unit 1830, the learning unit 1840 and the classification unit 1850 cooperate to provide a user with an optimized food heating result based on machine learning techniques as described above.

Herein, the processing unit 1820 and the learning unit 1840 are provided to reduce the amount of current sensor data of the above at least one sensor 1812. In particular, the learning unit 1840 is adapted to determine a mapping of current sensor data to current feature data by means of a variance analysis of at least one training heating process, to reduce the dimensionality of the current sensor data. The learning unit 1840 may be integrated in the monitoring apparatus 150 or may be an external unit located at another place, wherein a data connection may be provided, e.g. via Internet (as described below with regard to the usage of PCA-loops). The at least one training heating process may thus be based on current sensor data of the sensor unit 1810 of the local monitoring apparatus 150, but also be based on current sensor data of sensor units of further monitoring apparatuses at different places (on the world), provided the case the type of sensor data is comparable with each other. By means of training heating processes, the sensor data are reduced in dimensionality, wherein sensor data with the highest variance over time is weighted most.

The variance analysis performed by the learning unit 1840 comprises at least one of principal component analysis (PCA), isometric feature mapping (ISOMAP) or linear Discriminant analysis (LDA), or a dimensionality reduction technique, which have been described in all detail above.

An interpretation and selection of dominant features may thus be performed by applying PCA or principle component analysis to a sequence of food processing data. As described above in this way the features may be sorted by variance and the most prominent may be very beneficial for monitoring. By performing the analysis as described above, a mapping can be derived for mapping sensor data to feature data being reduced in dimensionality and being characteristic for the heating process being performed and being monitored by the monitoring apparatus 150. The mapping, which may be also received from an external server, or may be stored in a memory in the monitoring apparatus 150, is then applied by the processing unit 1820 to map the incoming current sensor data from the sensor unit 1810 to current feature data, which are then transmitted to the monitoring unit 1830. It is emphasized that in some cases, the "mapping" might be for some sensor data an identify mapping, thus some of the sensor data might be equal to the respective feature data, in particular with regard to pre-processed sensor data already containing characteristic values like the absolute temperature within the heating chamber, a volume value of the food to be heated, a humidity value of the humidity within the heating chamber. However, the mapping is preferably a mapping, in which the dimensionality of the data is reduced. The learning unit may be further adapted to determine a mapping of current feature data to feature data by means of a variance analysis of at least one training heating process to reduce the dimensionality of the current feature data.

The monitoring unit 1830 is then adapted to determine a current heating process state in a current heating process of monitored food by comparing the current feature data with reference feature data of a reference heating process.

During monitoring, one of the desired interests is to interpret the current feature data and arrive with a decision about regular and irregular processing. With the named method it is possible to collect features of regular behaviour and then assume irregular behaviour, once feature values differ from the previously learned regular behaviour. This may be supported by including classifiers such as Support Vector Machines or k-nearest neighbours as described above. The monitoring unit 1830 may be adapted to determine at least one action of at least one actuator based on the determined current feature data or current heating process state, wherein the control unit 1300 as described above may be implemented in the monitoring unit 1830. Thus, the monitoring unit 1830 may be adapted to execute all machine learning techniques as described above.

According to an embodiment, the reference feature data of a reference heating process is compared with current feature data to determine a current heating process state. The reference feature data may be predetermined data received from an external server or stored in a memory of the monitoring apparatus 150. In another embodiment, the learning unit 1840 (external or internal of the monitoring apparatus 150) may be adapted to determine reference feature data of a reference heating process by combining predetermined feature data of a heating program with a training set of feature data of at least one training heating process being classified as being part of the training set by an user. The heating program can be understood as a time dependent sequence of feature data being characteristic for a certain kind or type of food to be heated.

For example, a reference heating process or a predetermined heating program may be a sequence of feature data in time of a certain kind of food to be heated like a Croissant, which leads to an optimized heating or baking result. In other words, if the current feature data exactly follows the time dependent path of the reference feature data points in the feature space having the dimensionality of the number of chosen relevant features, the food will be heated in an optimized way after a predetermined optimized time, i.e. the Croissant will be baken perfectly. The optimized time may be dependent on the temperature within the heating or baking chamber.

Combining predetermined feature data of a heating program with a training set of feature data of at least one training heating process being classified as being part of the training set by an user means that a point cloud of feature data in the feature space of the training set (i.e. of at least one training heating process being considered as being "good" by a user) is averaged for each time point (a center point of the point cloud is determined within the feature space) and then used to adapt the predetermined heating program. This can be done by further averaging the features of the heating program and the features of the training set equally or in a weighted way for each time point. For example, the weighting of the training set may be 25%, the weighting for the predetermined heating program may be 75%.

Thus, at least one reference bake (training heating process) may be taken to optimize subsequent bakes. Further feedback from subsequent bakes may optimize the individual baking programs accordingly. Accordingly, it is possible to achieve more consistent baking quality, if the current bake is being adapted by the current sensor data and its calculated alterations taken from the difference of the current bake and the so called "ground truth" (reference heating process), which is the baking program (predetermined heating program) combined with the feature data of at least one reference bake (training set) as well as the feature data from later feed-back (training set) to the baking program and its according sensor data.

Thus, it is possible to calculate significant features with corresponding feature values from the sensor data of a reference bake combined with the time elapsed of the baking program. Here, it is feasible to use many different feature calculation variations and then sort them by variance. A possible mechanism to sort by variance is Principle Component Analysis (PCA) described above. When several features and feature values over time are calculated from a reference bake it is feasible to sort these sets of features and feature values over time with the PCA.

It is possible to automatically design a control algorithm for the repeating bakes by taking at least one of the most significant features and feature value data sets, preferably the one with most significant variance. If several reference bakes are present it is preferable to take the one with highest variance and highest feature value repetition.

To implement the above possibility to adapt the predetermined heating program to form a "ground truth", i.e. the reference heating process, the monitoring apparatus 150 may further comprise a recording unit 1822 to record current feature data of a current heating process, wherein the learning unit 1840 is adapted to receive the recorded feature data from the recording unit 1822 to be used as feature data of a training heating process.

The classification unit 1850 may be provided to classify the type of food to be heated. This may be done by image processing of an pixel image of the food to be heated, e.g. by face recognition techniques. After determining the type of food to be heated (bread roll, muffin, croissant or bread), the classification can be used to select a respective predetermined heating program or stored reference heating process corresponding to the respective type of food to be heated. In addition, sub-categories can be provided, for example small croissant, medium croissant, or big size croissant. Different reference heating processes may also stored with regard to non food type categories. For example, there may be a reference heating program corresponding to different time dependent environments or oven parameters.

For example, weather data may be implemented in the baking procedure of the present invention. By means of the known geographic altitude of the geometric position of the baking oven, the boiling point may be determined, thus leading to an adaption of the baking program. Moreover, local pressure, temperature, and humidity data of the environment of an oven may be used to further adapt the baking program. Thus, these data might be recorded and used as index data for certain reference heating programs, which then can be looked up in the memory.

Further, statistics of loads, units and corrections may also be used as data for the inventive self-learning baking procedure. Thus a baking data history may help to improve the baking procedure of the present invention. By means of the distributed feedback being accounted for by role definition, the baking process of the present invention may be improved. The heat treatment monitoring systems in use may be further displayed on a zoomable world map.

Moreover, the baking data history may also take into account the amount of baking products produced over time. The heat treatment monitoring system may search the baking data history for periodically occurring minima and maxima of the production and estimate the occurrence of the next minimum or maximum. The heat treatment monitoring system may then inform a user of the system whether too many or too little food is produced for the time period of the expected minimum or maximum.

The current heating process state is determined by comparing the current feature data with reference feature data. The comparing may be the determination of the distances of the current feature data and the reference feature data for each time point of the reference heating program. Thus, by determining the nearest distance of the determined distances, the time point of the nearest distance can be looked up in the reference heating program and thus, for example, a remaining baking time can be determined.

As described above, the sensor unit 1810 may comprise a camera like the camera 160 recording a pixel image of food being heated, wherein the current sensor data of the camera corresponds to the current pixel data of a current pixel image.

Feature detection for image processing may comprise the following steps: detection of edges, corners, blobs, regions of interest, interest points, processing of color or grey-level images, shapes, ridges, blobs or regions of interest or interest points. Feature from sensor data may also comprise target amplitude selection or frequency-based feature selection.

Herein, edges are points where there is a boundary (or an edge) between two image regions. In general, an edge can be of almost arbitrary shape, and may include junctions. In practice, edges are usually defined as sets of points in the image which have a strong gradient magnitude. Furthermore, some common algorithms will then chain high gradient points together to form a more complete description of an edge. These algorithms usually place some constraints on the properties of an edge, such as shape, smoothness, and gradient value. Locally, edges have a one dimensional structure.

The terms corners and interest points are used somewhat interchangeably and refer to point-like features in an image, which have a local two dimensional structure. The name "Corner" arose since early algorithms first performed edge detection, and then analysed the edges to find rapid changes in direction (corners). These algorithms were then developed so that explicit edge detection was no longer required, for instance by looking for high levels of curvature in the image gradient. It was then noticed that the so-called corners were also being detected on parts of the image which were not corners in the traditional sense (for instance a small bright spot on a dark background may be detected). These points are frequently known as interest points, but the term "corner" is used by tradition.

Blobs provide a complementary description of image structures in terms of regions, as opposed to corners that are more point-like. Nevertheless, blob descriptors often contain a preferred point (a local maximum of an operator response or a center of gravity) which means that many blob detectors may also be regarded as interest point operators. Blob detectors can detect areas in an image which are too smooth to be detected by a corner detector. Consider shrinking an image and then performing corner detection. The detector will respond to points which are sharp in the shrunk image, but may be smooth in the original image. It is at this point that the difference between a corner detector and a blob detector becomes somewhat vague. To a large extent, this distinction can be remedied by including an appropriate notion of scale. Nevertheless, due to their response properties to different types of image structures at different scales, the LoG and DoH blob detectors are also mentioned in the article on corner detection.

For elongated objects, the notion of ridges is a natural tool. A ridge descriptor computed from a grey-level image can be seen as a generalization of a medial axis. From a practical viewpoint, a ridge can be thought of as a one-dimensional curve that represents an axis of symmetry, and in addition has an attribute of local ridge width associated with each ridge point. Unfortunately, however, it is algorithmically harder to extract ridge features from general classes of grey-level images than edge-, corner- or blob features. Nevertheless, ridge descriptors are frequently used for road extraction in aerial images and for extracting blood vessels in medical images.

The current pixel data may comprise first pixel data corresponding to a first color, second pixel data corresponding to a second color, and third pixel data corresponding to a third color, wherein the first, second and third color corresponds to R,G and B, respectively. Herein, an illumination source for illuminating the food with white light is advantageous. It is, however, also possible to provide a monochromatic illumination source in a preferred wavelength area in the optical region, for example at 600 nm, to observe a grey pixel image in the respective wavelength.

Due to the provision of separate analysis of R, G and B pixel values, it is possible to implement an algorithm which may learn bread colors. Here, it is essential to segment the bread pixels from the oven pixels, which may be done by color. It is of advantage to use high dynamic range (HDR) pre-processed pictures to have more intensity information to have the best segmentation. Thus, the camera is preferably adapted to generate HDR processed pixel images as current pixel data. Herein, also logarithmic scaling may be implemented, wherein the camera is adapted to record a linear logarithmic or combined linear and logarithmic pixel images. To learn the bread pixels an Artificial Neural Network with back propagation or an SVM class as described above may be used, which are trained with pictures, where the oven is masked manually.

As an example, it may be that for baking rolls the most significant variance during the bake is a change in color (intensity change of pixels) and a change in volume (change in number of pixels with certain intensity). This may be the two most significant features during the reference bake or reference heating process and the corresponding feature values change over time. This creates a characteristic of the baking process. For instance the feature value representing the volume change may have a maximum after 10 minutes of 20 minutes and the color change after 15 minutes of 20 minutes of a bake. It is then possible to detect in repeating bakes by means of a classifier such as the aforementioned Support Vector Machine in the incoming sensor data of the repeating bake that the highest probabilities match in the reference bake or reference heating program. It may be that for instance the color change in the repeated bake has a maximum after 5 minutes for the volume change. The time difference of the repeating bake and the reference bake thus would be 50%. This would result in an adaptation of the remaining bake time by at least 50%. Here, an elapsing time of 5 minutes instead of 15.

Further, it may be possible to integrate an impact factor that may influence the impact of the control algorithm to the repeating baking program. This may be either automatically, such that the number of reference bakes influences the confidence factor, or such that it is manually set to a certain factor. This may as well be optimized by means of a remote system using information technology described earlier.

Moreover, it may be especially possible to change the temperature within this system by a change of a feature representing the color change. As it is described it is possible to calculate features representing the color change (change of intensity of pixels). It is feasible to normalize the pixel intensity. After normalization it is possible to adjust the temperature according to the change of color. If for example after 75% of remaining time there has not been the expected change in color the temperature may be risen, or if there has been more color change than expected from the reference bake the temperature may be lowered.

The monitoring apparatus 150 may further comprise a control unit 1860 adapted to change a heating process from a cooking process to a baking process based on a comparison of the current heating process state determined by the monitoring unit with a predetermined heating process state. The current heating process state is calculated as above by determining the time point of "nearest distance". By comparing the time points of the predetermined heating process state and the calculated time point, the heating process is changed, if the calculated time point is later then the time point of the predetermined heating process state. For example, as a rule of dumb, a proofing shall be finished after a volume change of 100% of the food to be heated, thus, if the bread roll or the Croissant has twice a volume, the proofing shall stop and the baking procedure shall start. The volume change of the bread or food to be baked may be detected by the camera pixel features in a very efficient way. The heat treatment machine to be controlled may be an integrated proofing/baking machine, however, also different machines for proofing or baking may also be controlled.

To simplify the calculations and to ensure repeatable results, it is preferred if the heating temperature is kept constant in a current heating process.

The control unit 1860 is further adapted to stop the heating process based on a comparison of the current heating process state determined by the monitoring unit with a predetermined heating process state corresponding to an end point of heating. The control unit 1860 may be adapted to alert a user, when the heating process has to be ended. Therefore, the monitoring apparatus may comprise an alert unit 1870 and a display unit 1880. The display unit 1880 is provided to indicate the current heating process state, for example the remaining heating or baking time. The display unit 1880 may further show a current pixel image of the inside of the heat treatment chamber for visual monitoring of the food to be heated by a user. The control unit 1860 may be adapted to control the display unit 1880 being adapted to indicate a remaining time of the heating process based on a comparison of the current heating process state determined by the monitoring unit with a predetermined heating process state corresponding to an end point of heating and/or to display images of the inside of the heat treatment chamber.

The control unit 1860 is further connected to an output interface 1890 for controlling actuators as described above or below like a temperature control of a heating chamber, means to adapt humidity in the heat treatment chamber by adding water, or a control of the ventilating mechanism (ventilating shutter). The actuators may further include means for adapting the fan speed, means for adapting the differential pressure between the heat treatment chamber and the respective environment, means for setting a time dependent temperature curve within the heat treatment chamber, means for performing and adapting different heat treatment procedures like proofing or baking, means for adapting internal gas flow profiles within the heat treatment chamber, means for adapting electromagnetic and sound emission intensity of respective electromagnetic or sound emitters for probing or observing properties of the food to be heated.

In particular, the control unit 1860 is adapted to control a temperature control of a heating chamber, means to adapt humidity in the heat treatment chamber by adding water or steam, a control of the ventilating mechanism, means for adapting the fan speed, means for adapting the differential pressure between the heat treatment chamber and the respective environment, means for setting a time dependent temperature curve within the heat treatment chamber, means for performing and adapting different heat treatment procedures like proofing or baking, means for adapting internal gas flow profiles within the heat treatment chamber, means for adapting electromagnetic and sound emission intensity of respective electromagnetic or sound emitters for probing or observing properties of the food to be heated.

A heat treatment monitoring method of the present invention comprises determining current sensor data of food being heated; determining current feature data from the current sensor data; and determining a current heating process state in a current heating process of monitored food by comparing the current feature data with reference feature data of a reference heating process. The method preferably further comprises determining a mapping of current sensor data to current feature data and/or to determine reference feature data of a reference heating process based on feature data of at least one training heating process. In addition, the method comprises determining a mapping of current sensor data to current feature data by means of a variance analysis of at least one training heating process to reduce the dimensionality of the current sensor data. The method further comprises determining a mapping of current feature data to feature data by means of a variance analysis of at least one training heating process to reduce the dimensionality of the current feature data. The variance analysis preferably comprises at least one of principal component analysis (PCA), isometric feature mapping (ISOMAP) or linear Discriminant analysis (LDA), or a dimensionality reduction technique. The method further comprises preferably determining reference feature data of a reference heating process by combining predetermined feature data of a heating program with a training set of feature data of at least one training heating process being classified as being part of the training set by an user. In addition, by the method of the present invention, current feature data of a current heating process may be recorded, wherein the recorded feature data is used as feature data of a training heating process. Furthermore, the method may comprise classifying the type of food to be heated and to choose a reference heating process corresponding to the determined type of food. Preferably, a heating process is changed from a proofing process to a baking process based on a comparison of the current heating process state with a predetermined heating process state. The heating temperature is preferably kept constant in a current heating process. Preferably, the heating process is stopped based on a comparison of the current heating process state determined by the monitoring unit with a predetermined heating process state corresponding to an end point of heating. In an advantageous embodiment, a user is alerted, when the heating process has to be ended.

According to another embodiment of the monitoring apparatus 150, machine learning may be used for a multi input and multi output (MIMO) system. In particular, an adjusting system for added water, remaining baking time and/or temperature may be implemented by a heat treatment monitoring system using machine learning techniques.

The system is collecting all sensor data during the reference bake. In case of humidity, at least one hygrometer detects a reference value for the humidity over bake time during the reference bake. When repeating a baking of the same product the amount of water to be added may be different. The amount of baked products may be different, the oven inside volume may be different, or there may be more or less ice or water on the baked products when loading the oven.

Next to other adaptations, the control system according to the invention adds as much water as needed to achieve similar conditions compared to the reference baking. As the remaining bake time may be adapted by the control system, the time at which the water will be added changes as well. Instead of using a fixed time, such as to add 1 liter of water after 10 minutes of a 20 minutes baking program, according to this embodiment the system will add as much water as needed to hit the reference bake humidity level after 50% of elapsed time.

Once irregular behaviour is recognized in an implementation of this invention, this signal or irregularity and it's corresponding amplitude may be used to adjust processing devices such as mixers (energy induced into dough), dough dividers (cutting frequency), or industrials ovens (baking program times or temperature) within a food production process.

According to another embodiment the observation of the food within the baking chamber may be done "live", thus a live view of the oven inside enables a remote access of the baking process. Also remote oven adjustment may be possible to improve the baking behavior of a self-learning heat treatment monitoring system.

In an embodiment "perception", "cognition", and "action" (P-C-A) loops, cognitive agents, and machine learning techniques suitable for industrial processes with actuators and intelligent sensors may be used. Transferring cognitive capabilities, knowledge, and skills, as well as creating many interacting P-C-A loops will be advantageous in a cognitive factory.

Only very few food production processes are unique. The majority of food production processes run at different facilities or at different times performing identical tasks in similar environments. Still, often no or limited information exchange exists between these processes. The same food processing stations often require an individual configuration of every entity managing similar process tasks. In order to increase the capability of machines to help each other it is advantageous to combine in space or time distributed P-C-A loops. Certain topics arise to approach this aim: In order to enable skill transfer between different entities it is advantageous to establish a reliable and adaptable Multi-P-C-A-loop topology. This meta-system should be able to identify similar processes, translate sensor data, squire features, and analyze results of the different entities. Dimensionality reduction, clustering, and classification techniques may enable the machines to communicate on higher levels. Machine-machine trust models, collective learning, and knowledge representation are essential for this purpose. Furthermore some industrial processes may be redefined to optimize the overall performance in cognitive terms. Both data processing and hardware configuration should result in a secure, reliable, and powerful procedure to share information and transfer skills.

Using self-optimizing algorithms for control or parameterization of industrial applications offers the possibility to continuously improve the individual knowledge base. Reinforcement learning, for instance, gives a set of methods that provide this possibility. These algorithms rely on exploration in the processes state-space in order to learn the optimal state-action combinations. A reinforcement learning agent can also be described by a simple P-C-A-Loop, where the process of evaluating the state information of the environment is the "perception" element of the loop, the alteration of current control laws represents the "action" part and the process of mapping estimated state information to new control laws gives the "cognition" section of the single P-C-A loop. In industrial applications exploring a large state-space is not always feasible for various reasons like safety, speed, or costs. Using the Multi-P-C-A-Loop approach for distributing the learning task over multiple agents, can reduce the amount of exploration for the individual agents, while the amount of learning experience still remains high. It furthermore enables teaching among different P-C-A loops. A possible assignment for the Multi-P-C-A approach is the combination of multiple agents in one system or assembly line, for instance a monitoring and a closed-loop control unit. Two different agents could be trained for optimization of different process parameters. The combination of both on a Multi-P-C-A level could be used to find an optimal path for all parameters.

Both outlined Multi-P-C-A-Loops may improve manufacturing performance in setup and configuration times, process flexibility as well as quality. One approach combines and jointly improves similar workstations with joint knowledge and skill transfer. The other enables different units to self-improve with each others feed-back. In the following, a networking system for cognitive processing devices according to the present invention should be described. It is an advantage of the present invention, that, once the collaborative systems gain enough machine knowledge, they avoid repetitive configuration steps and may significantly reduce down times as well as increase product flexibility.

According to one embodiment of the present invention, in order to facilitate the integration of several heat treatment monitoring systems 100, all distributed systems are connected to each other via Internet. The knowledge gained by these systems is shared, thus allowing a global database of process configurations, sensor setups and quality benchmarks.

In order to share information between machines, all of them have to use a similar method of feature acquisition. As a first scenario to achieve these goals using cognitive data processing approaches for combining the input data from multiple sensors of the respective sensor units 1810 of the monitoring systems 100 in order to receive a good estimation of the state the process is currently in.

Using cognitive dimensionality reduction techniques, unnecessary and redundant data from these sensors can be removed. The reduced sensor data is used to classify the state of the process. Clustering allows for identification of specific process states, even between different set-ups. If a significant difference from the references, and therefore an unknown process condition, is detected, the supervisor will be alerted. The expert can then teach the new state and countermeasures (if possible) to the system in order to improve its performance.

The cognitive system to be developed should be able to learn to separate acceptable and unacceptable results and furthermore be able to avoid unacceptable results where possible. The usage of technical cognition eliminates the need for a complete physical model of the baking or food production process. The system is able to stabilize the process by improving at least one steering variable. Distributed cognition allows for a central database between different manufacturing locations. The information gathered from one process can be transferred to a similar process at a different location.

What is claimed is:

1. A system, comprising a computer, the computer comprising a processor and a memory, the memory storing instructions executable by the processor, the instructions including instructions to:
   identify a plurality of first pixel data received at a first time as representing a food item;
   determine respective first colors for respective first pixels of the first pixel data;
   identify a plurality of second pixel data that is received at a second time as representing the food item being treated by a heat treatment machine, the second pixel data including second pixels corresponding to respective first pixels in the first plurality of pixel data, whereby the second time is a current time;
   determine respective second colors for respective second pixels of the second pixel data;
   output a current temperature of the heat treatment machine based on differences between the first colors and the second colors at the first and second times; and
   output an adjusted temperature of the heat treatment machine based on the differences between the first colors and the second colors at the first and second times.

2. The system of claim 1, the instructions further including instructions to output the adjusted temperature based on determining distances in an observation space of the current temperature to a reference temperature for the first time and a reference temperature for the second time.

3. The system of claim 2, the instructions further including instructions to determine the current time by determining a time point of reference data having a nearest distance to the current feature temperature.

4. The system of claim 1, the instructions further comprising instructions to determine a remaining time of heating the food item based on comparing the second pixel data to reference pixel data representing an end of a heating process.

5. The system of claim 1, the instructions further comprising instructions to classify a type of the food item and to select reference data for the current temperature based on the type of the food item.

6. The system of claim 1, wherein the first and second pixel data include data identifying a first color component, a second color component, and a third color component.

7. The system of claim 1, wherein the current temperature is output from a machine learning program that is trained with heating process data including pixel colors for a food item type of the food item at specified times and temperatures at the respective times for a type of the heat treatment machine.

8. The system of claim 1, the instructions further comprising instructions to apply a mapping to the first and second pixel data that is derived by a variance analysis that reduces a dimensionality of the pixel data.

9. The system of claim 8, wherein the variance analysis includes applying a highest weight to pixel data having a highest variance.

10. The system of claim 1, further comprising a camera communicatively coupled with the computer, and arranged to acquire the first and second pixel data via an infrared filter.

11. The system of claim 1, the instructions further comprising instructions to apply logarithmic scaling to the first pixel data and the second pixel data.

12. The system of claim 1, wherein the food item is in the heat treatment machine at the first time.

13. The system of claim 1, wherein the food item is pre-baked or raw at the first time.

* * * * *